(12) United States Patent
Vidhani et al.

(10) Patent No.: US 11,034,655 B1
(45) Date of Patent: Jun. 15, 2021

(54) COMPOUNDS FOR INHIBITING THE ACTIVITY OF SARS-COV-2 SPIKE GLYCOPROTEIN

(71) Applicants: Anupkumar Vinod Vidhani, Vadodara (IN); Dinesh Vinod Vidhani, Hollywood, FL (US)

(72) Inventors: Anupkumar Vinod Vidhani, Vadodara (IN); Dinesh Vinod Vidhani, Hollywood, FL (US)

( * ) Notice: Subject to any disclaimer, the term of this patent is extended or adjusted under 35 U.S.C. 154(b) by 0 days.

(21) Appl. No.: 16/988,692

(22) Filed: Aug. 9, 2020

(51) Int. Cl.
  *C07D 211/72* (2006.01)
  *C07C 307/02* (2006.01)
  *C07D 309/28* (2006.01)

(52) U.S. Cl.
  CPC .......... *C07D 211/72* (2013.01); *C07C 307/02* (2013.01); *C07D 309/28* (2013.01)

(58) Field of Classification Search
  None
  See application file for complete search history.

(56) References Cited

FOREIGN PATENT DOCUMENTS

JP          200763202    *  3/2007

OTHER PUBLICATIONS

Li, Q.; Guan, X.; Wu, P.; Wang, X.; Zhou, L; Tong, Y.; Ren, R.; Leung, K.S.M.; Lau, E.H.Y.; Wong, J.Y.; Xing, X.; Xiang, N.; Wu, Y.; Li, C.; Chen, Q.; Li, D.; Liu, T.; Zhao, J.; Liu, M.; Tu, W.; Chen, C.; Jin, L.; Yang, R.; Wang, Q.; Zhou, S.; Wang, R.; Liu, H.; Luo, Y.; Liu, Y.; Shao, G.; Li,,H.; Tao, Z.; Yang, Y.; Deng, Z.; Liu, B.; Ma, Z.; Zhang, Y.; Shi, G.; Lam, T.T.Y.; Wu, J.T.; Gao G,F.; Cowling, B.J.; Yang, B.; Leung, G.M.; Feng, Z. N Engl J Med. 2020, 382, 1199-1207.
Tian, X.; Li, C.; Huang, A.; Xia, S.; Lu, S.; Shi, Z.; Lu, L.; Jiang, S.; Yang, Z.; Wu, Y.; Ying, T. Emerg Microbes Infect. 2020, 9, 382-385.
Jiang S, Hillyer C, Du L. Trends Immunol. 2020, 41, 355-359.
Huang, C.; Wang, Y.; Li, X.; Ren, L.; Zhao, J.; Hu, Y.; Zhang, L.; Fan, G.; Xu, J.; Gu, X, Cheng, Z.; Yu, T.; Xia, J.; Wei, Y.; Wu, W.; Xie, X.; Yin, W.; Li, H.; Liu, M.; Xiao, Y.; Gao, H.; Guo, L.; Xie, J.; Wang, G.; Jiang, R.; Gao, Z.; Jin, Q.; Wang, J.; Cao, B. Lancet. 2020, 395, 497-506.
Xu, H.; Zhong, L; Deng, J.; Peng, J.; Dan, H.; Zeng, X.; Li, T.; Chen, Q. Int J Oral Sci. 2020, 12, 8.
Zou, X.; Chen, K.; Zou, J.; Han, P.; Hao, J.; Han, Z.; Front. Med. 2020, 14, 185-192.
Tai, W; He, L.; Zhang, X.; Jing, P.; Voronin, D.; Jiang, S.; Zhou, Y.; Du, L. Cell Mol Immunol. 2020, 17, 613-620.
Rabi, F. A.; Al Zoubi, M. S.; Kasasbeh, G. A.; Salameh, D. M.; Al-Nasser, A. D. Pathogens. 2020, 9, 231.

Wrapp, W.; Wang, N.; Corbett, K. S.; Goldsmith, J. A.; Hsieh, C. L.; Abiona, O.; Graham, B. S.; McLellan, J. S. Science 2020, 367, 1260-1263.
Hackbart, M.; Deng, X.; Baker, S. C. Proc. Natl. Acad. Sci. U.S.A. 2020, 117, 8094-8103.
Volk, A.; Hackbart, M.; Deng, X.; Cruz-Pulido, Y.; O'Brien, A.; Baker, S. C. J. Virol. 2020, 94, 1-14.
VanBlargan, L. A.; Goo, L.; Pierson, T. C. Microbiol. Mol. Biol. Rev. 2016, 80, 989-1010.

(Continued)

*Primary Examiner* — Po-Chih Chen

(57) ABSTRACT

The present invention relates to compounds of formula (I) and its analogues (II) and (III): in which $R_1$-$R_{14}$, X, Y, $Z_1$-$Z_4$ are in the Summary of the Invention; capable of inhibiting the activity of RBD of SARS-COV-2 in its "closed" conformation before it binds with the human ACE2 receptor. The invention further provides a process for the preparation of compounds of the invention.

3 Claims, 9 Drawing Sheets

(56) References Cited

OTHER PUBLICATIONS

Rossmann, M. G. J. Biol. Chem. 1989, 264, 14587-14590.
Kwong, P.D.; Doyle, M.L.; Casper, D.J.; Cicala, C.; Leavitt, S.A.; Majeed, S.; Steenbeke, T.D.; Venturi, M.; Chaiken, I.; Fung, M.; Katinger, H.; Parren, P.W.I.H.; Robinson, J.; Van Ryk, D.; Wang, L.; Burton, D.R.; Freire, E.; Wyatt, R.; Sodroski, J.; Hendrickson, WA.; Arthos, J. Nature, 2002, 420, 678-682.
Vigerust, D. J.; Shepherd, V. L. Trends Microbiol. 2007, 15, 211-218.
Fehr, A. R.; Perlman, S. Methods Mol Biol. 2015, 1282, 1-23.
Walls, A. C.; Park, Y.J.; Tortorici, M. A.; Wall, A.; McGuire, A. T.; Veesler, D. Cell. 2020, 181, 281-292.
Simmons, G.; Zmora, P.; Gierer, S.; Heurich, A.; Pohlmann, S. Antiviral Res. 2013, 100, 605-614.
Sungnak, W.; Huang, Ni.; Bécavin, C.; Berg, M.; Queen, R; Litvinukova, M.; Talavera-López, C.; Maatz, H.; Reichart, D.; Sampaziotis, F.; Worlock, K. B.; Yoshida, M.; Barnes, J. L; HCA Lung Biological Network. Nat Med, 2020, 26, 681-687.
Li, F. Annu. Rev. Virol. 2016, 3, 237-261.
Du, L.; He, Y.; Zhou, Y.; Liu, S.; Zheng, B-J.; Jiang, S. Nat Rev Microbiol. 2009, 7, 226-236.
Du, L.; Tai, W.; Yang, Y.; Zhao, G.; Zhu, Q.; Sun, S.; Liu, C.; Tao, X.; Tseng, C-T. K; Perlman, S.; Jiang, S.; Zhou, Y.; Li, F. Nat Commun. 2016, 7, 13473.
Mayer, S.; Daigle, D. M.; Brown, E. D.; Khatri, J.; Organ, M. G. J. Comb. Chem. 2004, 6, 776-782.
Sun, Y.; Gu, J.; Wang, H.; Sessler, J. L; Thordarson, P.; Lin, Y-J.; Gong, H. J. Am. Chem. Soc. 2019, 141, 20146-20154.
Luo, T. Y.; Liu, C.; Gan, X. Y.; Muldoon, P. F.; Diemler, N. A.; Millstone, J. E.; Rosi, N. L. J. Am. Chem. Soc. 2019, 141, 2161-2168.
Li, W.; Xiao, G.; Deng, G.; Liang, L. Org. Chem. Front., 2018, 5, 1488-1492.
Xu, Y.; Liu, X.; Chen, W.; Deng. G.; Liang, Y. Org. Chem. 2018, 83, 22, 13930-13939.
Kalgutkar, R. S.; Lahti, P. M. Tetrahedron Lett. 2003, 44, 2625-2628.
Ramón, R. S.; Bosson, J.; Díez-Gonzalez, S.; Marion, N.; Nolan, S. P. J. Org. Chem., 2010, 75, 1197-1202.
Blair, A.; Stevenson, L.; Dewar, D.; Pimlottc, S. L.; Sutherland, A. Med. Chem. Commun, 2013, 4, 1461-1466.
Peressin, N.; Adamski, M.; Schibli, E. M.; Ye, E.; Frisken, B. J.; Holdcroft, S. Macromolecules 2020, 53, 3119-3138.
Rami, F.; Bächtle, F.; Plietker, B. Catal. Sci. Technol., 2020, 10, 1492-1497.
Than, T-G.; Zhou, T. Y.; Lin, F.; Zhang, L.; Zhou, C.; Qi, Q. Y.; Li, Z-T.; Zhao, X. Org. Chem. Front., 2016, 3, 1635-1645.
Nanasawa, M.; Miwa, M.; Hirai, M.; Kuwabara, T. J. Org. Chem., 2000, 65, 593-595.
Paoletta, S.; Tosh, D. K.; Finley, a.; Gizewski, E. T.; Moss, S. M.; Gao, Z-G.; Auchampach, J. A.; Salvemini, D.; Jacobson, K. A. J. Med. Chem. 2013, 56, 5949-5963.
McDermott, T. S.; Bhagavatula, L.; Borchardt, T. B.; Engstrom, K. M.; Gandarilla, J.; Kotecki, B. J.; Kruger, A. W.; Rozema, M. J.; Sheikh, A. Y.; Wagaw, S. H.; Wittenberger, S_ J. Org. Process Res. Dev. 2009, 13, 1145-1155.
Tahmouresilerd, B.; Moody, M.; Agogo, L.; Cozzolino, A. F. Dalton Trans., 2019, 48, 6445-6454.
Feng, H-X.; Wang, Y-Y.; Chen, J.; Zhou, L. Adv. Synth. Catal. 2015, 357, 940-944.
Hall, H. K.; Nogues, P.; Rhoades, J. W.; Sentman, R. C.; Detar, M. J. Org. Chem. 1982, 47, 1451-1455.
Erfurt, K; Wandzik, I.; Walczak, K.; Matuszek, K.; Chrobok, A. Green Chem., 2014, 16, 3508-3514.
Brown, P. A.; Bonnert, R. V.; Jenkins, P. R.; Selim, M. R. Tetrahedron Lett. 1987, 28, 693-696.
Bures, F.; Cvejn, D.; Melánová,K.; Beneš, L; Svoboda, J.; Zima, V.; Pytela, O.; Mikysek, T.; Růžičková, Z.; Kityk, I. V.; Wojciechowskif, A.; AlZayed, N. J. Mater. Chem. C, 2016, 4, 468-478.
Gooseman, N. E. J.; O'Hagan, D.; Peach, M. J. G.; Slawin, A M. Z.; Tozer, D. J.; Young, R. J. Angew. Chem. Int. Ed. 2007, 46, 5904-5908.
Afarinkia, K.; Bearpark, M. J.; Ndibwami, A. J. Org. Chem. 2005, 70, 1122-1133.
Carothers, W. H.; Collins, A. M.; Kirby, J. E. J. Am. Chem. Soc. 1933, 55, 786-788.
Pauff, S. M.; Miller, S. C. J. Org. Chem. 2013, 78, 711-716.
Behroz, I.; Durkin, P.; Gratz, S.; Seidel, M.; Rostock, L.; Spinczyk, M.; Weston, J. B.; Süssmuth, R. D. Chem. Eur. J. 2019, 25, 16538-16543.
Hendrickson, J. B. J. Am. Chem. Soc. 1962, 84, 653-659.
Kheirabadi, M.; Creech, G. S.; Qiao, J. X.; Nirschl, D. S.; Leahy, D. K.; Boy, K. M.; Carter, P. H.; Eastgate, M. D. J. Org. Chem. 2018, 83, 4323-4335.

\* cited by examiner

A
"Closed" or "lying down" conformation:
RBD hidden from immune system

B
"Open" or "standing up" conformation:
RBD ready to bind with human ACE2

COMPOUNDS FOR INHIBITING THE ACTIVITY OF SARS-COV-2 SPIKE GLYCOPROTEIN

FIELD OF THE INVENTION

The present invention generally relates to compounds capable of inhibiting the activity of SARS-COV-2 spike glycoprotein. More specifically, these compounds demonstrate a very strong binding affinity for the receptor binding domain (RBD) of spike glycoprotein attached on SARS-COV-2 virus.

BACKGROUND OF THE INVENTION

Corona virus disease 2019 (COVID-19) is a respiratory illness cause by the severe acute respiratory syndrome corona virus 2 (SARS-COV-2) and is responsible for COVID-19 pandemic. See: (a) Li, Q.; Guan, X.; Wu, P.; Wang, X.; Zhou, L.; Tong, Y.; Ren, R.; Leung, K. S. M.; Lau, E. H. Y.; Wong, J. Y.; Xing, X.; Xiang, N.; Wu, Y.; Li, C.; Chen, Q.; Li, D.; Liu, T.; Zhao, J.; Liu, M.; Tu, W.; Chen, C.; Jin, L.; Yang, R.; Wang, Q.; Zhou, S.; Wang, R.; Liu, H.; Luo, Y.; Liu, Y.; Shao, G.; Li, H.; Tao, Z.; Yang, Y.; Deng, Z.; Liu, B.; Ma, Z.; Zhang, Y.; Shi, G.; Lam, T. T. Y.; Wu, J. T.; Gao G, F.; Cowling, B. J.; Yang, B.; Leung, G. M.; Feng, Z. *N Engl J Med.* 2020, 382, 1199-1207; (b) Guo, Y-R.; Cao, Q-D.; Hong, Z-S.; Tan, Y-Y.; Chen, S-D.; Jin, H-J.; Tan, K-S.; Wang, D-Y.; Yan, Y. *Military Med Res,* 2020, 7, 1-10; and (c) Tian, X.; Li, C.; Huang, A.; Xia, S.; Lu, S.; Shi, Z.; Lu, L.; Jiang, S.; Yang, Z.; Wu, Y.; Ying, T. *Emerg Microbes Infect.* 2020, 9, 382-385.

Like other corona viruses, the SARS-COV-2 consists of four major structural proteins known as spike (S), envelope (E), membrane (M) and nucleocapsid (N). See: (a) Jiang S, Hillyer C, Du L. *Trends Immunol.* 2020, 41, 355-359; and (b) Huang, C.; Wang, Y.; Li, X.; Ren, L.; Zhao, J.; Hu, Y.; Zhang, L.; Fan, G.; Xu, J.; Gu, X, Cheng, Z.; Yu, T.; Xia, J.; Wei, Y.; Wu, W.; Xie, X.; Yin, W.; Li, H.; Liu, M.; Xiao, Y.; Gao, H.; Guo, L.; Xie, J.; Wang, G.; Jiang, R.; Gao, Z.; Jin, Q.; Wang, J.; Cao, B. *Lancet.* 2020, 395, 497-506.

Among the four major proteins, S-glycoprotein is a homotrimeric transmembrane protein composed of S1 and S2 domains that protrudes out from the viral envelope. The receptor binding domain (RBD) of Si plays a key role in facilitating entry of the virus in the host cell by with the angiotensin-converting enzyme 2 (ACE2) of the host. A strong binding is reported to takes place between human and bat ACE2 receptors at the residues 331-524 of S1-domain. Furthermore, RBD of SARS-COV-2 has significantly higher binding affinity for human ACE2 receptor compared to the RBD of SARS-COV.

The ACE2 receptor is extensively expressed in the alveolar cells (AT2) of the lungs, myocardial cells, absorptive enterocytes from the colon and ileum, upper esophagus cholangiocytes, kidney proximal tubule cells etc. Thus, patients infected with SARS-COV-2 not only show respiratory distress but also display the symptoms of heart, kidney and digestive tract disorders. See: (a) Xu, H.; Zhong, L.; Deng, J.; Peng, J.; Dan, H.; Zeng, X.; Li, T.; Chen, Q. *Int J Oral Sci.* 2020, 12, 8; and (b) Zou, X.; Chen, K.; Zou, J.; Han, P.; Hao, J.; Han, Z.; *Front. Med.* 2020, 14, 185-192.

In contrast to SARS-COV, the cryo-EM studies revealed that the RBD of SARS-COV-2 is in "lying-down" or "closed state" and is activated by the host protease. See: (a) Tai, W.; He, L.; Zhang, X.; Jing, P.; Voronin, D.; Jiang, S.; Zhou, Y.; Du, L. Cell *Mol Immunol.* 2020, 17, 613-620; (b) Rabi, F. A.; Al Zoubi, M. S.; Kasasbeh, G. A.; Salameh, D. M.; Al-Nasser, A. D. *Pathogens.* 2020, 9, 231; and (c) Wrapp, W.; Wang, N.; Corbett, K. S.; Goldsmith, J. A.; Hsieh, C. L.; Abiona, O.; Graham, B. S.; McLellan, J. S. *Science* 2020, 367, 1260-1263.

Among two major immuno-evasive strategies viz., conformational masking and glycan shielding, the SARS-COV-2 adopts a conformational masking tactic to hide its RBD from the immune surveillance. The "lying-down" conformation is thus critical to evade the immune response from the host. See (a) Hackbart, M.; Deng, X.; Baker, S. C. *Proc. Natl. Acad. Sci. U.S.A.* 2020, 117, 8094-8103; (b) Volk, A.; Hackbart, M.; Deng, X.; Cruz-Pulido, Y.; O'Brien, A.; Baker, S. C. *J. Virol.* 2020, 94, 1-14; (c) VanBlargan, L. A.; Goo, L.; Pierson, T. C. *Microbiol. Mol. Biol. Rev.* 2016, 80, 989-1010; (d) Rossmann, M. G. *J. Biol. Chem.* 1989, 264, 14587-14590; (e) Kwong, P. D.; Doyle, M. L.; Casper, D. J.; Cicala, C.; Leavitt, S. A.; Majeed, S.; Steenbeke, T. D.; Venturi, M.; Chaiken, I.; Fung, M.; Katinger, H.; Parren, P. W. I. H.; Robinson, J.; Van Ryk, D.; Wang, L.; Burton, D. R.; Freire, E.; Wyatt, R.; Sodroski, J.; Hendrickson, W. A.; Arthos, J. *Nature,* 2002, 420, 678-682; and (f) Vigerust, D. J.; Shepherd, V. L. *Trends Microbiol.* 2007, 15, 211-218.

Despite the inactive "closed" or "lying-down" conformation, it is believed that the RBD of SARS-COV-2 maintains a high infectivity by undergoing the host protease-triggered conformational change to the "stand-up" position. This "stand-up" position is believed to bind strongly with the human ACE-2 receptor. Next, the furin-like protease on the exterior of the host cells cleaves S1-S2 domains followed by further cleavage of S2 domain (S2' site). These events expose membrane fusion peptides. See: (a) Shang, J.; Wan, Y.; Luo, C.; Ye, G.; Geng, Q.; Auerbach, A.; Li, F. *Proceedings of the National Academy of Sciences* 2020, 117, 11727-11734; (b) Fehr, A. R.; Perlman, S. *Methods Mol Biol.* 2015, 1282, 1-23; (c) Walls, A. C.; Park, Y. J.; Tortorici, M. A.; Wall, A.; McGuire, A. T.; Veesler, D. *Cell.* 2020, 181, 281-292; (d) Rabi, F. A.; Al Zoubi, M. S.; Kasasbeh, G. A.; Salameh, D. M.; Al-Nasser, A. D. *Pathogens.* 2020, 9, 231. (e) Simmons, G.; Zmora, P.; Gierer, S.; Heurich, A.; Pöhlmann, S. *Antiviral Res.* 2013, 100, 605-614. (f) Sungnak, W.; Huang, Ni.; Bécavin, C.; Berg, M.; Queen, R.; Litvinukova, M.; Talavera-López, C.; Maatz, H.; Reichart, D.; Sampaziotis, F.; Worlock, K. B.; Yoshida, M.; Barnes, J. L.; HCA Lung Biological Network. *Nat Med,* 2020, 26, 681-687; and (g) Li, F. *Annu. Rev. Virol.* 2016, 3, 237-261.

Thus, to combat COVID-19, it is imperative to prevent the entry of virus into the host cell by inhibiting the most immunogenic region, the hidden RBD of SARS-COV-2. But the "lying down" conformation not only helps virus to evade immune surveillance but also poses a major challenge in drug therapy. See (a) Du, L.; He, Y.; Zhou, Y.; Liu, S.; Zheng, B-J.; Jiang, S. *Nat Rev Microbiol.* 2009, 7, 226-236; and (b) Du, L.; Tai, W.; Yang, Y.; Zhao, G.; Zhu, Q.; Sun, S.; Liu, C.; Tao, X.; Tseng, C-T. K.; Perlman, S.; Jiang, S.; Zhou, Y.; Li, F. *Nat Commun.* 2016, 7, 13473.

The compounds of present invention are predicted to inhibit the entry of SARS-COV-2 by forming a strong complex with the otherwise inaccessible, hidden, "lying-down" conformation of the RBD.

SUMMARY OF THE INVENTION

In one aspect, the present invention is directed to compounds of formula (I).

[Chemical structure of formula (I) showing a molecule with substituents $R_1$ through $R_{13}$, $Z_1$-$Z_4$, X and Y]

in which:

X is selected from a group consisting of biguanidine, biguanidinium ion, biguanidinium dication, guanidine, guanidnium, amine, ammonium ion, aminoalkyl, alkylammonium ion, amide, urea, amino, and hydroxyl;

Y is selected from a group consisting of methylene, methine, oxygen and amine;

$R_1$ is selected from a group consisting of hydrogen, methyl, aminomethyl and hydroxymethyl;

$R_2$ is selected from a group consisting of carboxylic acid, carboxylate ion, sulfonic acid, sulfonate ion, amide and sulfonamide;

$R_3$ is selected from a group consisting of carboxylic acid, carboxylate ion, sulfonic acid, sulfonate ion, amide and sulfonamide;

In one of the preferred embodiments, $R_2$ and $R_3$ groups are cis relative to each other;

$R_4$, $R_5$, $R_6$, and $R_7$ at each occurrence are independently selected from the group consisting of hydrogen, halogen (i.e., fluoro, chloro, bromo, iodo), amino, $C_{1-12}$ alkylamino, $C_{1-12}$ alkylammonium salts, alkoxy, hydroxyl, $C_{6-24}$ aryl, $C_{3-12}$ cycloalkyl, $C_{1-12}$ alkyl, cyano and $C_{3-18}$ heteroaryl. The alkyl, aryl, cycloalkenyl, heteroaryl, amino, and alkylamino groups may be unsubstituted. The alkylamino and alkylammonium salts may be primary, secondary, or tertiary;

$R_8$ is selected from the group consisting of buta-1,3-diyne-1-sulfonamide, penta-2,4-diynamide, hydrogen, halogen (i.e., fluoro, chloro, bromo, iodo), amino, $C_{1-12}$ alkylamino, $C_{1-12}$ alkylammonium salts, alkoxy, hydroxyl, $C_{6-24}$ aryl, $C_{3-12}$ cycloalkyl, $C_{1-12}$ alkyl, cyano and $C_{3-18}$ heteroaryl. The alkyl, aryl, cycloalkenyl, heteroaryl, amino, and alkylamino groups may be unsubstituted. The alkylamino and alkylammonium salts may be primary, secondary, or tertiary;

$R_9$-$R_{11}$ at each occurrence are independently selected from a group consisting of is selected from the group consisting of hydrogen, halogen (i.e., fluoro, chloro, bromo, iodo), amino, $C_{1-12}$ alkylamino, $C_{1-12}$ alkylammonium salts, alkoxy, hydroxyl, $C_{6-24}$ aryl, $C_{3-12}$ cycloalkyl, $C_{1-12}$ alkyl, cyano, $C_{3-18}$ heteroaryl, and hydroxyalkyl. The alkyl, aryl, cycloalkenyl, heteroaryl, amino, and alkylamino groups may be unsubstituted. The alkylamino and alkylammonium salts may be primary, secondary, or tertiary;

$R_{12}$ and $R_{13}$ are independently selected from a group consisting of hydrogen, methyl, hydroxy, amino, aminoalkyl and hydroxyalkyl;

$Z_1$-$Z_4$ at each occurrence are independently selected from a group consisting of nitrogen and carbon atoms;

One example of the preferred embodiment, shown below, displays a strong in-silico binding with the "closed" or "lying down" conformation of SARS-COVID-2 RBD (FIG. 1);

Other objects and features will be in part apparent and in part pointed out hereinafter.

BRIEF DESCRIPTION OF THE DRAWINGS

FIG. 5. Synthetic strategy to access compounds of structure 27a.

DETAILED DESCRIPTION OF THE EMBODIMENT(S) OF THE INVENTION

Figure 1:
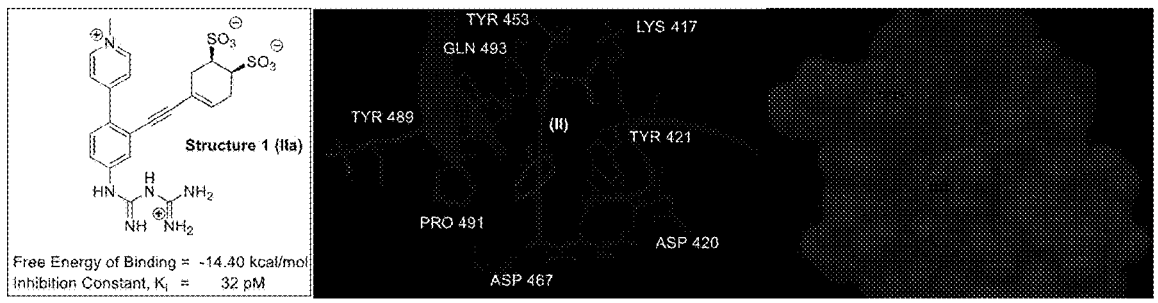
FIG. 1. Figure on the left shows the binding free energy and binding constant of compound having structure 1 (IIa). The middle and right figures show the binding site of structure 1(IIa) on the closed conformation of SARS-COV-2 RBD.
Figure 2:
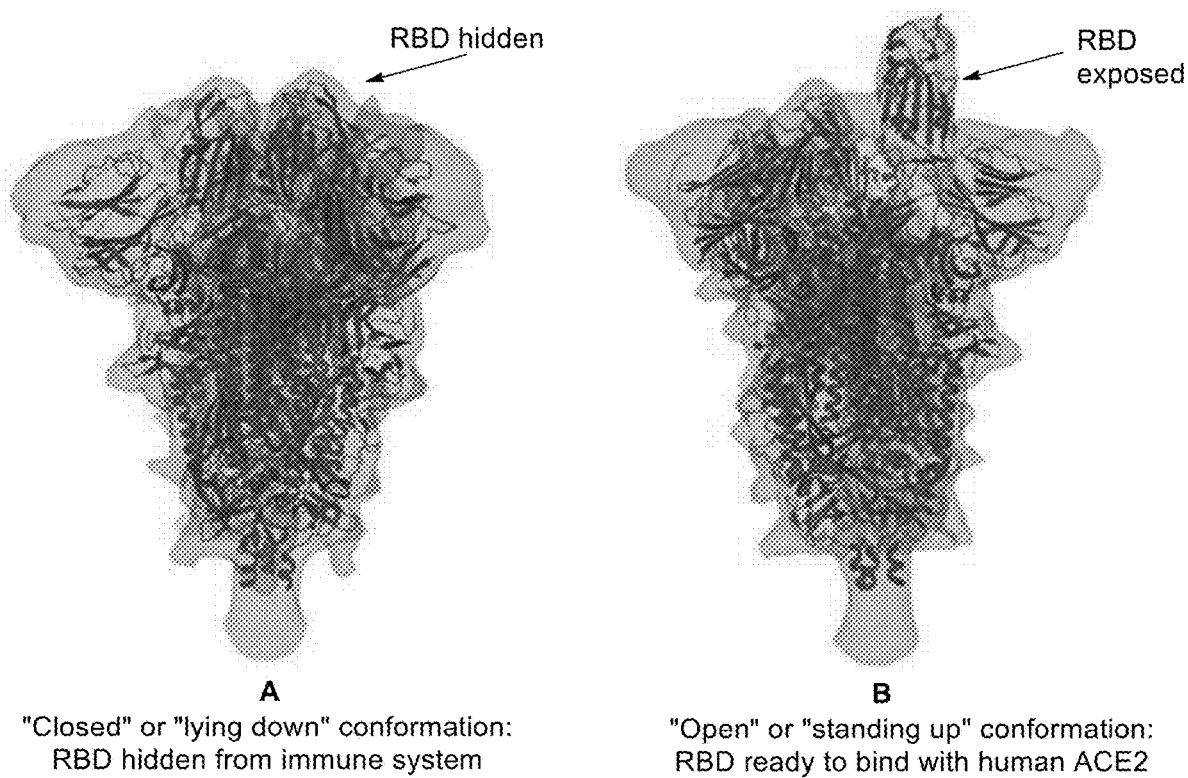
FIG. 2. Figure A corresponds to "closed" or "lying down" conformation of SARS-COV-2 RBD (PDB ID: 6VXX). Figure B corresponds to "open" or "standing up" conformation of SARS-COV-2 RBD (PDB ID: 6VYB).

The present invention relates to compounds capable with the "closed" or "lying down" conformation of SARS-COV-2 RBD of spike protein and inhibit the binding of spike protein to the human ACE2 receptor (FIG. 2).

Closed state provides access to only Gly446, Tyr449, Ala475, Phe486, Asn487, Tyr489, Gln493, Gly496, Gln498, Thr500, Asn501, and Gly502 amino acid residues whereas Lys417, Tyr453, Leu455, Phe456, and Tyr505 are hidden from the solvent as well as potential inhibitors.

The compounds of the present invention not only bind strongly with the accessible amino acid residues Tyr 489 and Gln 493 but also with the hidden residues Lys 417 and Tyr 453 in the "closed" conformation.

In one embodiment of compounds of the invention, are the compounds of formula (I):

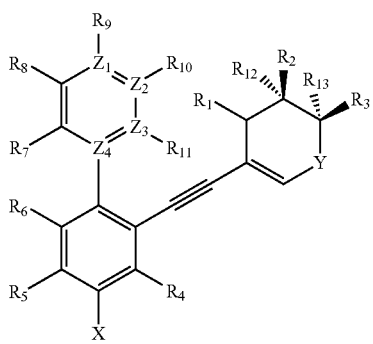

(I)

in which:
X is selected from a group consisting of biguanidine, biguanidinium ion, biguanidinium dication, guanidine, guanidnium, amine, ammonium ion, aminoalkyl, alkylammonium ion, amide, urea, amino, and hydroxyl;
Y is selected from a group consisting of methylene, methine, oxygen and amine;
$Z_1$-$Z_4$ at each occurrence are independently selected from a group consisting of nitrogen and carbon atoms;
$R_1$ is selected from a group consisting of hydrogen, methyl, amino and hydroxy;
$R_2$ and $R_3$ are independently selected from a group consisting of carboxylic acid, carboxylate ion, sulfonic acid, sulfonate ion, amide and sulfonamide; in one of the preferred embodiments, $R_2$ and $R_3$ groups are cis relative to each other;
$R_4$, $R_5$, $R_6$, and $R_7$ at each occurrence are independently selected from the group consisting of hydrogen, halogen (i.e., fluoro, chloro, bromo, iodo), amino, $C_{1-12}$ alkylamino, $C_{1-12}$ alkylammonium salts, alkoxy, hydroxyl, $C_{6-24}$ aryl, $C_{3-12}$ cycloalkyl, $C_{1-12}$ alkyl, cyano and $C_{3-18}$ heteroaryl; the alkyl, aryl, cycloalkenyl, heteroaryl, amino, and alkylamino groups with respect to $R_4$, $R_5$, $R_6$, and $R_7$ may be unsubstituted; the alkylamino and alkylammonium salts with respect to $R_4$, $R_5$, $R_6$, and $R_7$ may be primary, secondary, or tertiary;
$R_8$ is selected from the group consisting of buta-1,3-diyne-1-sulfonamide, penta-2,4-diynamide, hydrogen, halogen (i.e., fluoro, chloro, bromo, iodo), amino, $C_{1-12}$ alkylamino, $C_{1-12}$ alkylammonium salts, alkoxy, hydroxyl, $C_{6-24}$ aryl, $C_{3-12}$ cycloalkyl, $C_{1-12}$ alkyl, cyano and $C_{3-18}$ heteroaryl; the alkyl, aryl, cycloalkenyl, heteroaryl, amino, and alkylamino groups with respect to $R_8$ may be unsubstituted; the alkylamino and alkylammonium salts with respect to $R_8$ may be primary, secondary, or tertiary;
$R_9$-$R_{11}$ at each occurrence are independently selected from a group consisting of is selected from the group consisting of hydrogen, halogen (i.e., fluoro, chloro, bromo, iodo), amino, $C_{1-12}$ alkylamino, $C_{1-12}$ alkylammonium salts, alkoxy, hydroxyl, $C_{6-24}$ aryl, $C_{3-12}$ cycloalkyl, $C_{1-12}$ alkyl, cyano, $C_{3-18}$ heteroaryl, and hydroxyalkyl; the alkyl, aryl, cycloalkenyl, heteroaryl, amino, and alkylamino groups may be unsubstituted; the alkylamino and alkylammonium with respect to $R_9$-$R_{11}$ salts may be primary, secondary, or tertiary;
$R_{12}$ and $R_{13}$ are independently selected from a group consisting of hydrogen, methyl, hydroxy, amino, aminoalkyl and hydroxyalkyl.

In a further embodiment are compounds of formula (II):

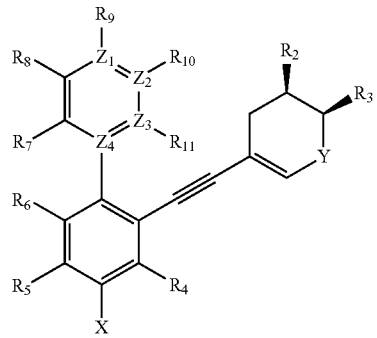

(II)

in which: X, Y, $Z_1$-$Z_4$, $R_2$-$R_{11}$ have been defined with respect to structure (I);

In a further embodiment are compounds of formula (IIa):

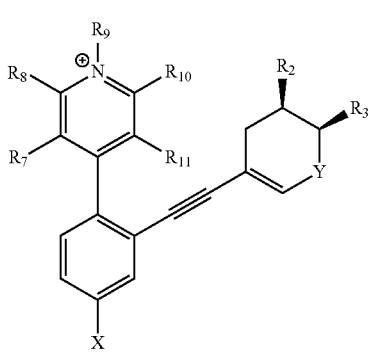

(IIa)

in which: X, Y, $R_2$, $R_3$, and $R_7$-$R_{11}$ have been defined with respect to structure (I);

In a further embodiment are compounds selected from:

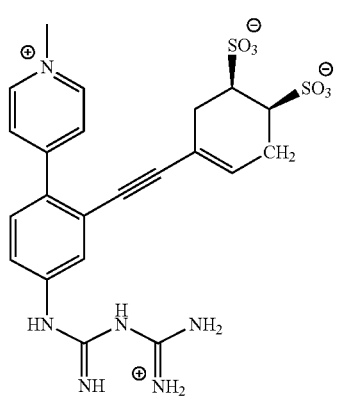

1

2
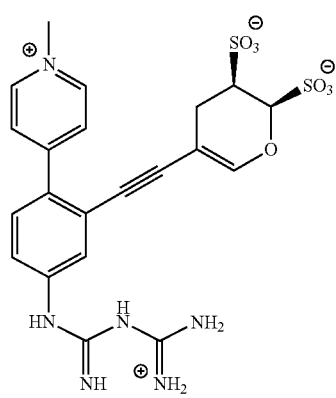
3
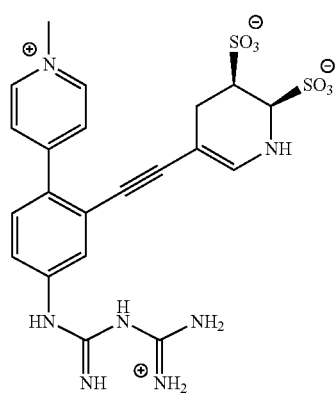
4
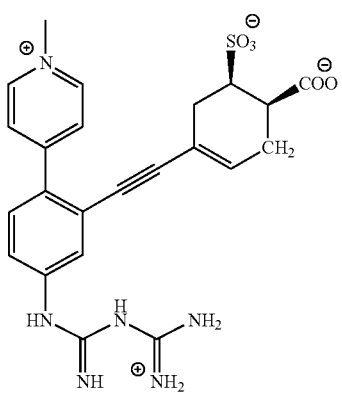
5
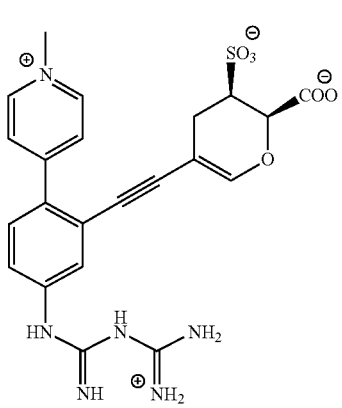
6
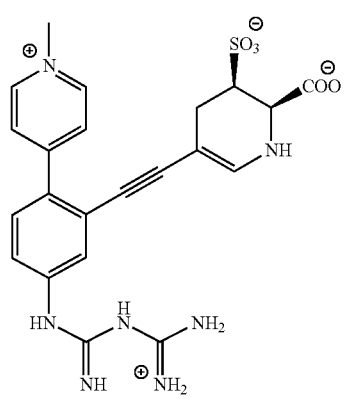
7
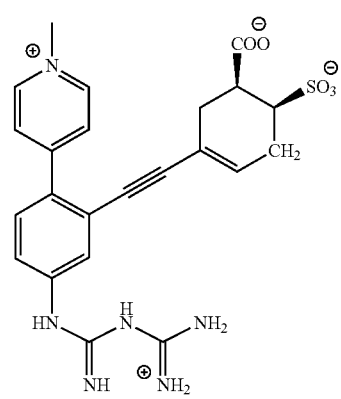
8
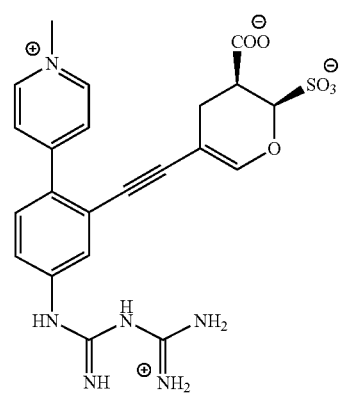
9
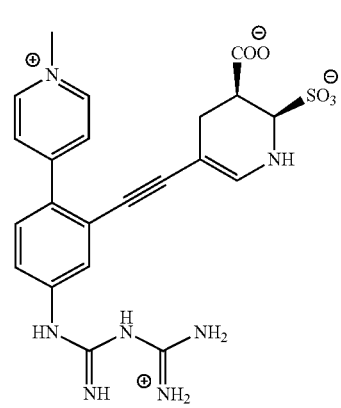

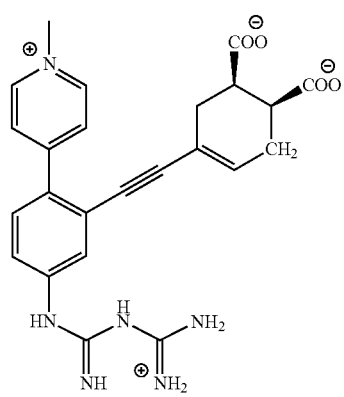
10
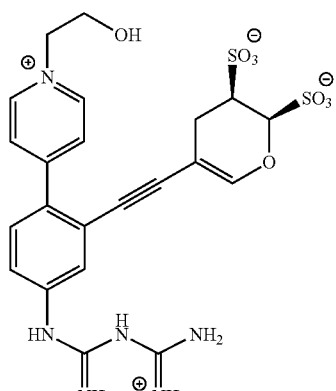
14
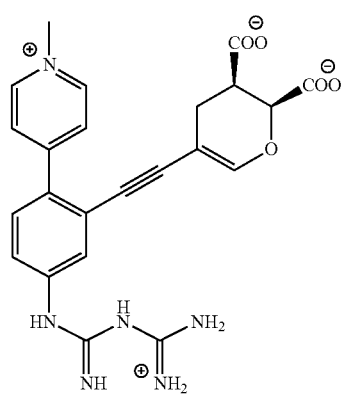
11
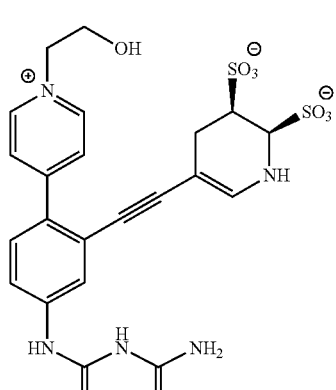
15
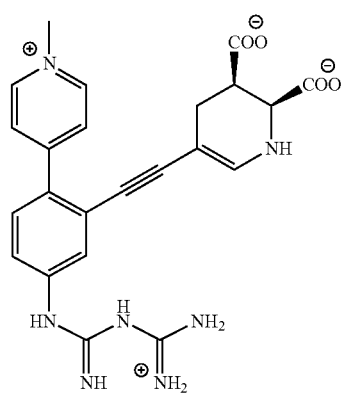
12
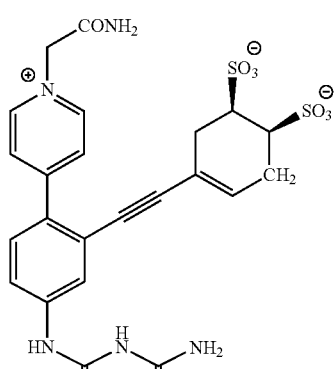
16
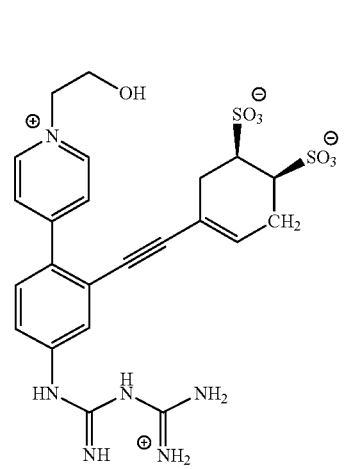
13
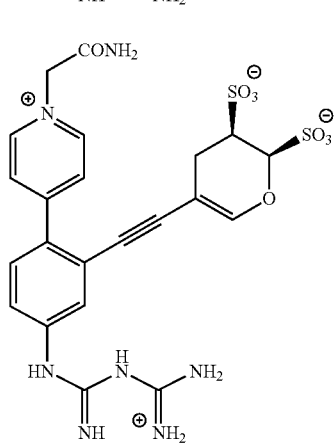
17

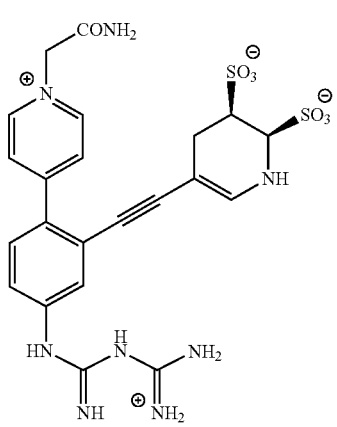

Figure 3:
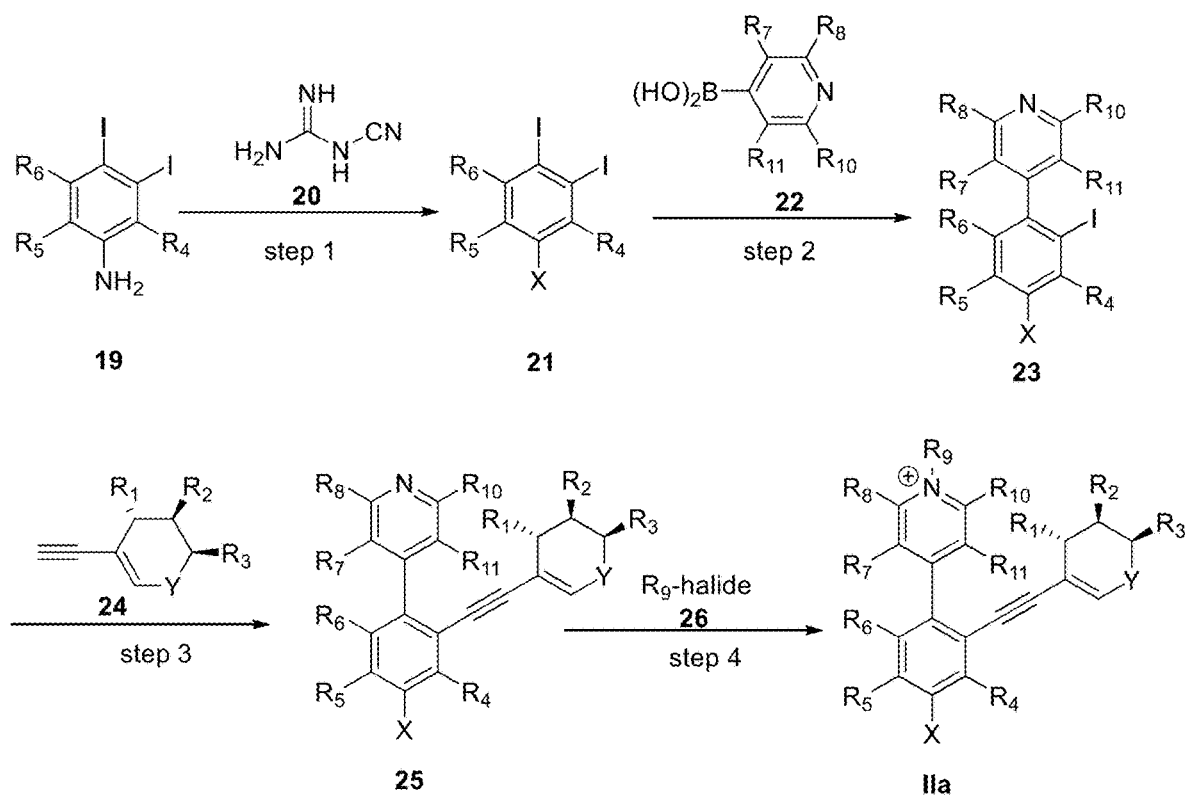
FIG. 3. Synthetic strategy to access compounds of structure IIa.

In some embodiments, the compounds with structure (IIa) may synthesized according to the following sequence: reacting compounds having structure (19) and a dicyandiamide having structure (20) in presence of concentrated hydrochloric acid results into compounds having structure (21); reacting compounds having structure (21) with arylboronic acid having structure (22) in presence palladium catalysts results into compounds having structure (23); reacting compounds having structure (23) with compounds having structure (24) in presence of palladium and copper catalysts results into compounds having structure (25); reacting compounds having structure (25) with alkyl halides having general formula $R_9$-halide (26) followed by hydrolysis results into compounds having formula IIa (FIG. 3).

Figure 4:
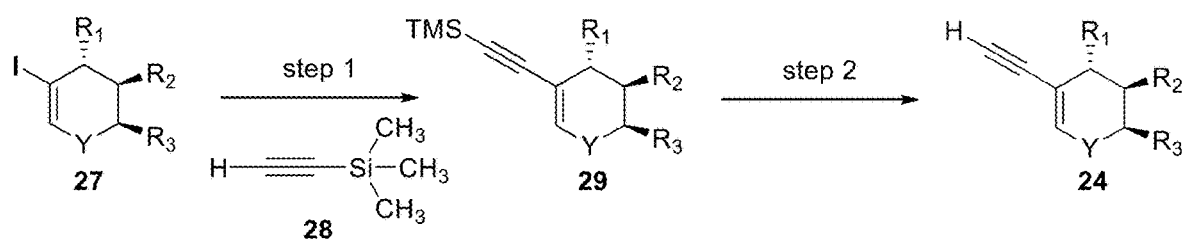
FIG. 4. Synthetic strategy to access compounds of structure 24.

In one embodiment of compounds of the invention, the compounds of formula (24) are synthesized according to the following sequence: reacting compound having structure 27 with compounds having structure 28 in presence of palladium and copper iodide catalysts results into compound having structure 29; reacting compounds having structure 29 with a base results into structure 24 (FIG. 4).

Figure 5:
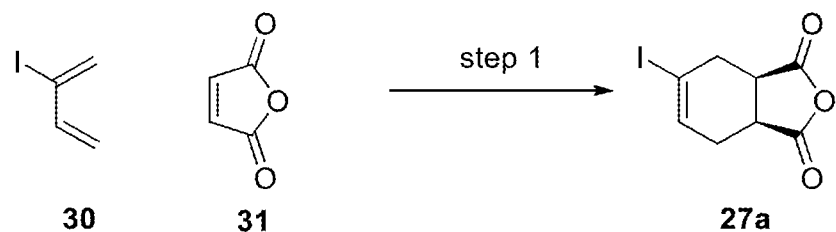

In one embodiment of compounds of the invention, the compounds of formula (27) are synthesized according to the following sequence: reacting compound having structure 30 with compound having structure 31 results into compound having structure 27a (FIG. 5).

Figure 6:
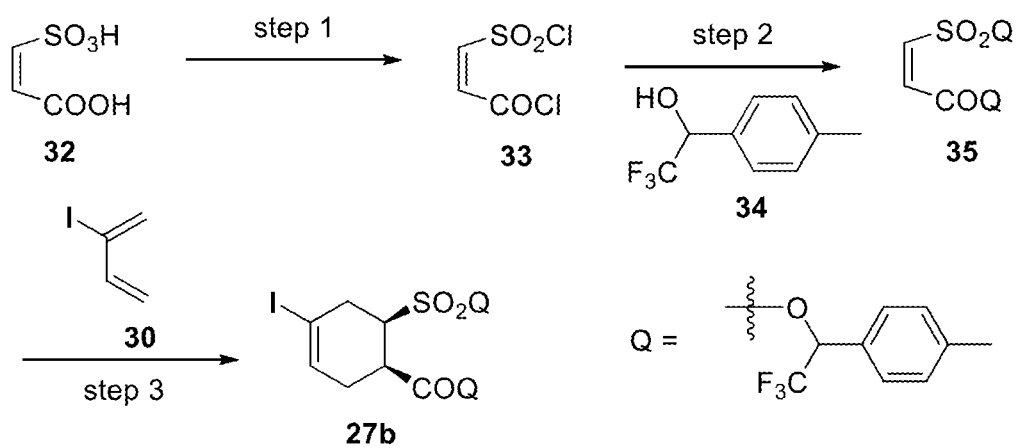
FIG. 6. Synthetic strategy to access compounds of structure 27b.

In one embodiment of compounds of the invention, the compounds of formula (27) are synthesized according to the following sequence: reacting compound having structure 32 with thionyl chloride ($SOCl_2$) and catalytic amount of dimethyl formamide (DMF) under inert atmosphere ($N_2$ or Ar) results into compound having structure 33; reacting compounds having structure 33 with compound having structure 34 results into compound having structure 35; reacting compound having structure 35 with compound having structure 30 results into compound having structure 27b (FIG. 6).

Figure 7:
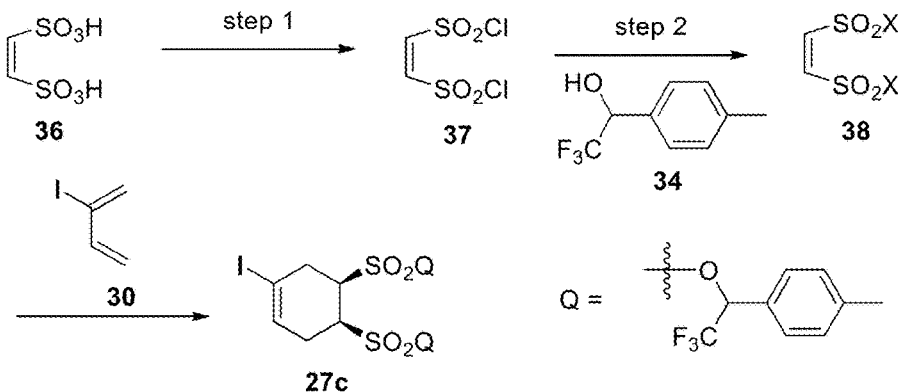
FIG. 7. Synthetic strategy to access compounds of structure 27c.

In one embodiment of compounds of the invention, the compounds of formula (27) are synthesized according to the following sequence: reacting compound having structure 36 with thionyl chloride ($SOCl_2$) results into compound having structure 37; reacting compounds having structure 37 with compound having structure 34 results into compound having structure 38; reacting compound having structure 38 with compound having structure 30 results into compound having structure 27c (FIG. 7).

In a further embodiment with respect to structure II, are the compounds of formula (IIb):

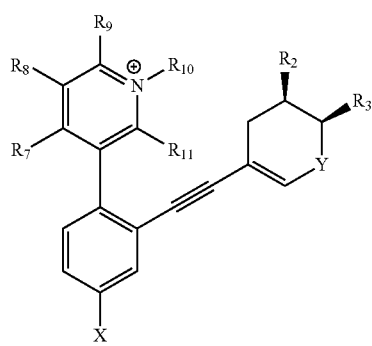

in which: X, Y, $R_2$, $R_3$, and $R_7$-$R_{11}$ have been defined with respect to structure (I);

In a further embodiment with respect to compounds with formula IIb are compounds selected from:

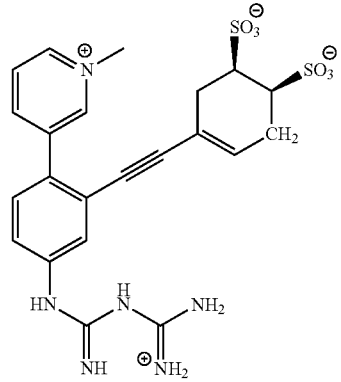

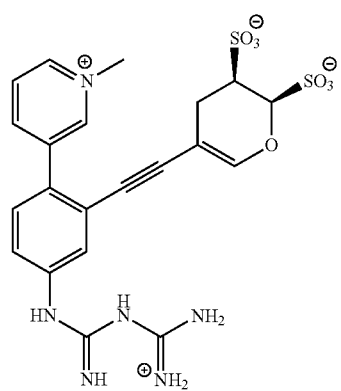

Figure 8:
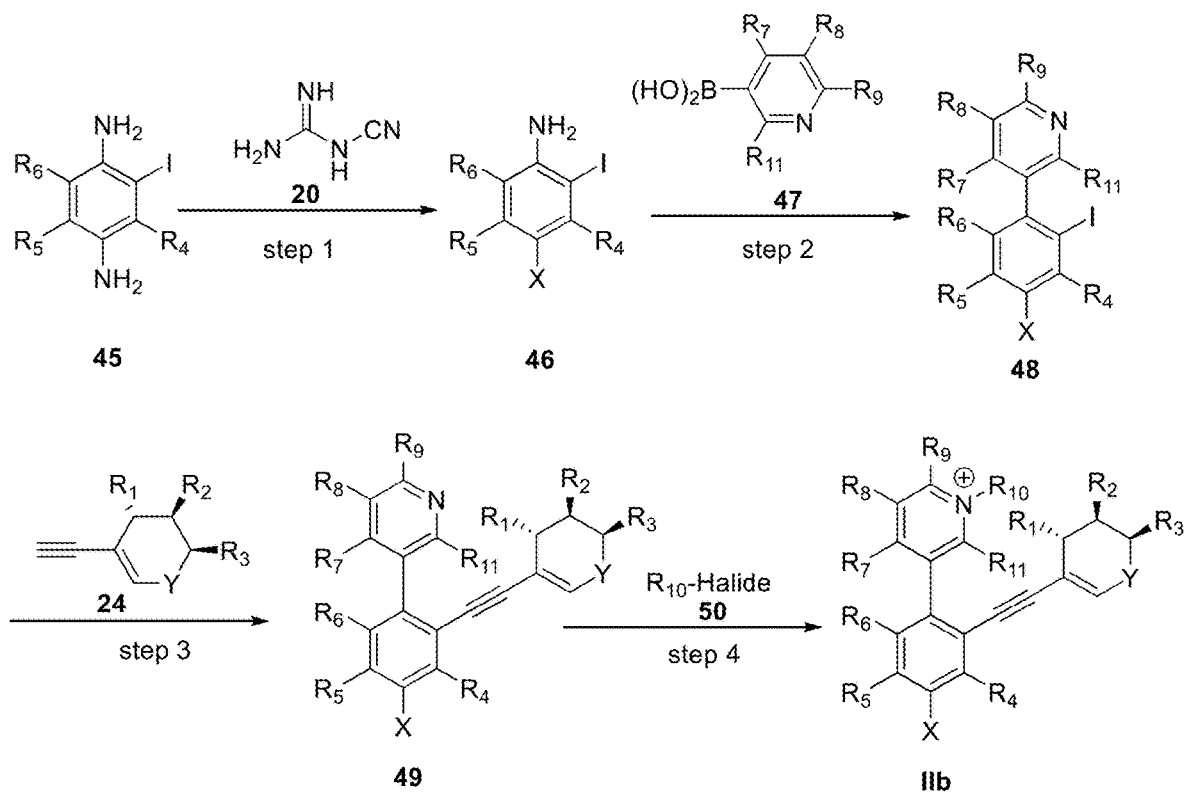
FIG. 8. Synthetic strategy to access compounds of structure IIb.

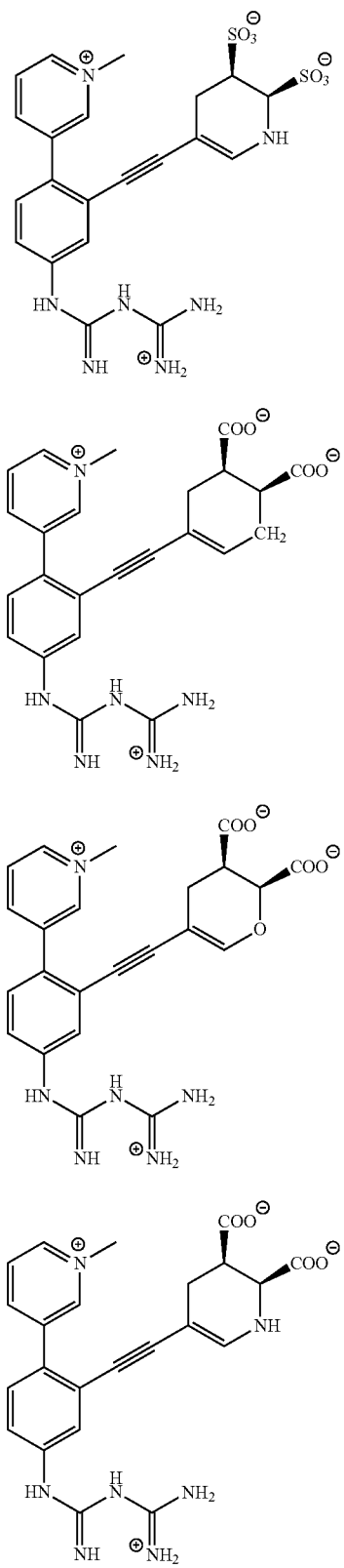

having structure (20) in presence of concentrated hydrochloric acid results into compounds having structure (46); reacting compounds having structure (46) with arylboronic acid having structure (47) in presence palladium catalysts results into compounds having structure (48); reacting compounds having structure (48) with compounds having structure (24) in presence of palladium and copper catalysts results into compounds having structure (49); reacting compounds having structure (49) with alkyl halides having general formula $R_{10}$-halide (50) followed by hydrolysis results into compounds having formula IIb (FIG. 8).

In a further embodiment are compounds of formula (IIc):

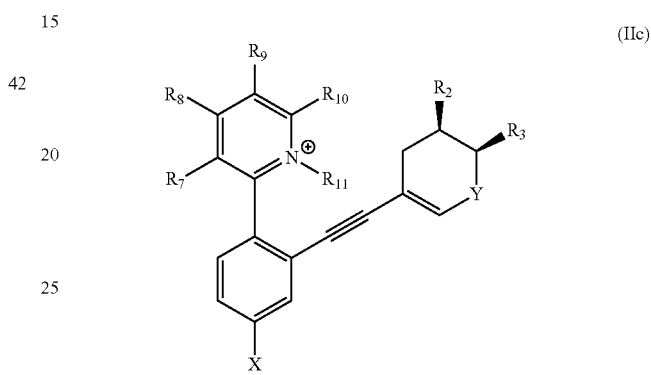

in which: X, Y, $R_2$, $R_3$, and $R_7$-$R_{11}$ have been defined with respect to structure (I);

In a further embodiment with respect to compounds with formula IIc are compounds selected from:

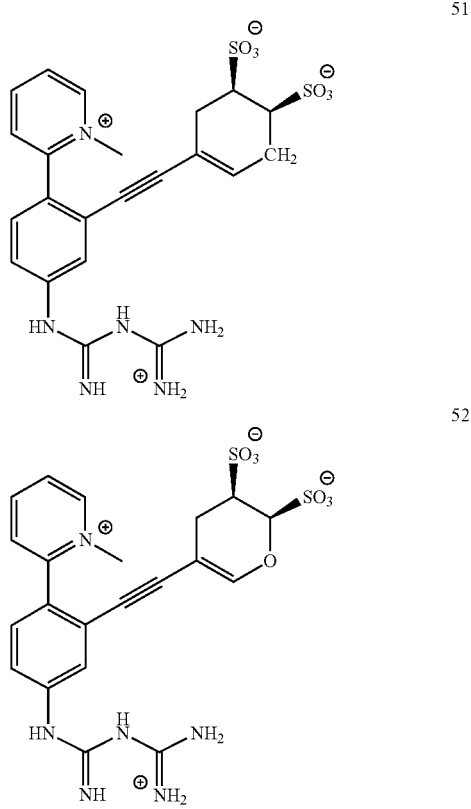

In some embodiments, the compounds with structure (IIb) may synthesized according to the following sequence: reacting compounds having structure (45) and a dicyandiamide -continued 53
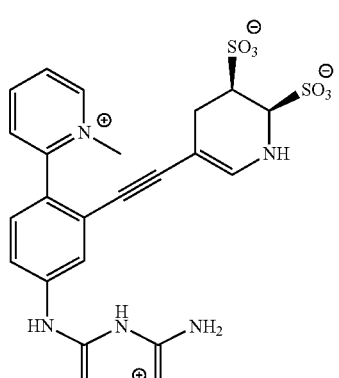

54
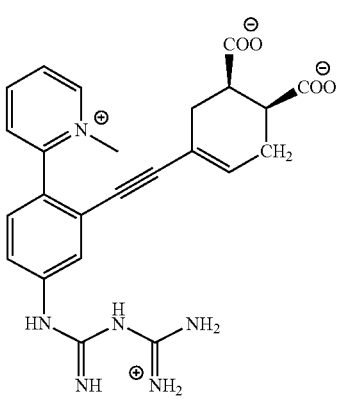

55
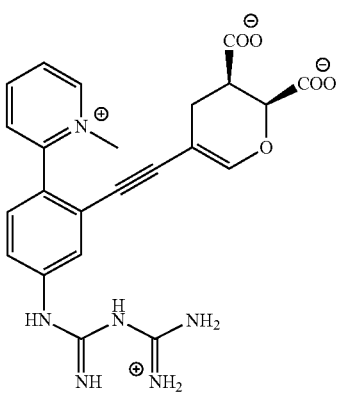

56
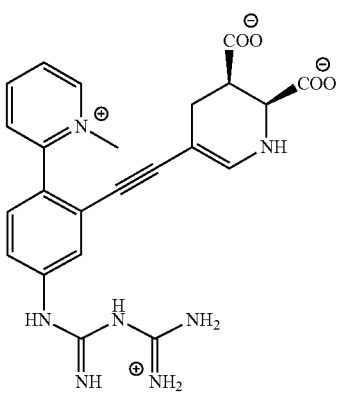

Figure 9:
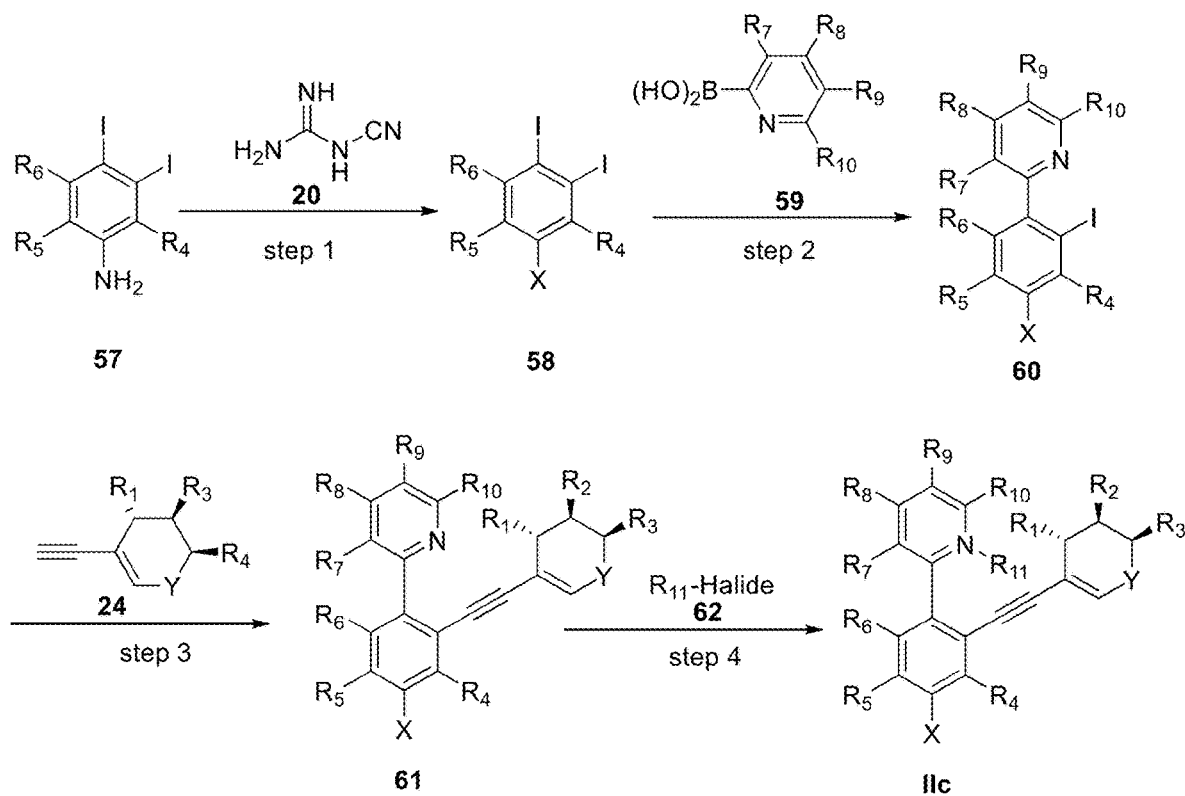
FIG. 9. Synthetic strategy to access compounds of structure IIc.

In some embodiments, the compounds with structure (IIc) may synthesized according to the following sequence: reacting compounds having structure (57) and a dicyandiamide having structure (20) in presence of concentrated hydrochloric acid results into compounds having structure (58); reacting compounds having structure (58) with arylboronic acid having structure (59) in presence palladium catalysts results into compounds having structure (60); reacting compounds having structure (60) with compounds having structure (24) in presence of palladium and copper catalysts results into compounds having structure (61); reacting compounds having structure (61) with alkyl halides having general formula $R_{11}$-halide (62) followed by hydrolysis results into compounds having formula IIc (FIG. 9).

In a further embodiment are compounds of formula (IId):

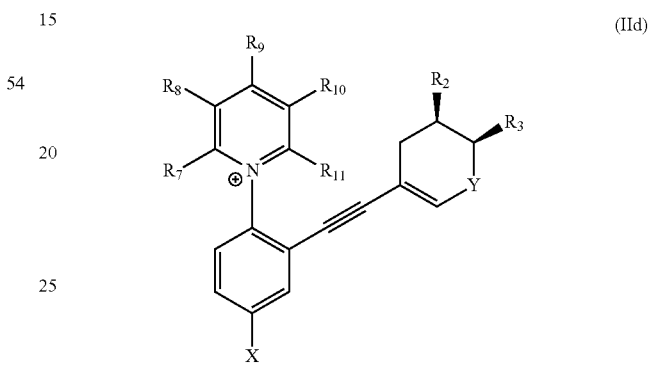

(IId)

in which: X, Y, $R_2$, $R_3$, and $R_7$-$R_{11}$ have been defined with respect to structure (I);

In a further embodiment with respect to compounds with formula IId are compounds selected from:

63
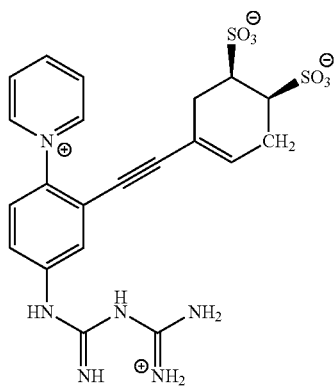

64
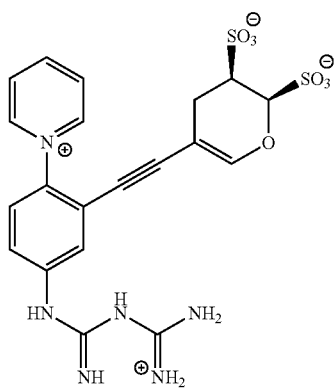

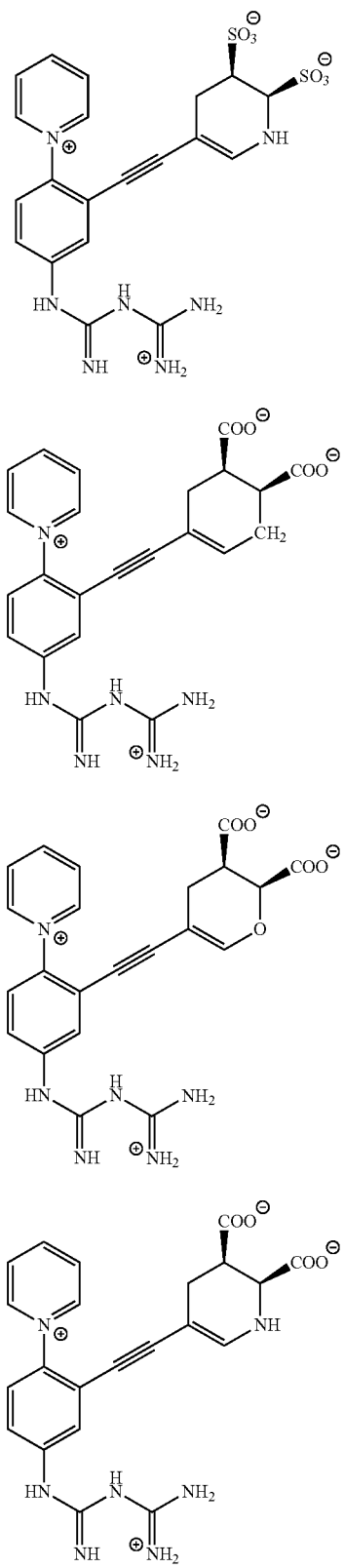

Figure 10:
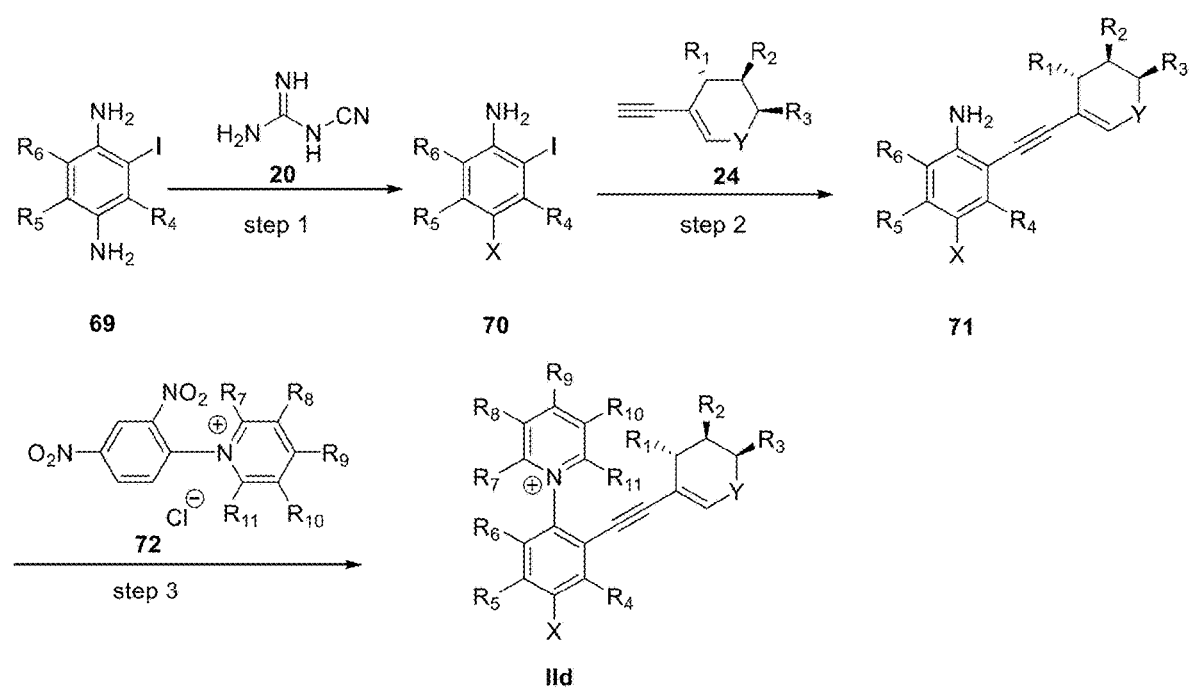
FIG. 10. Synthetic strategy to access compounds of structure IId.

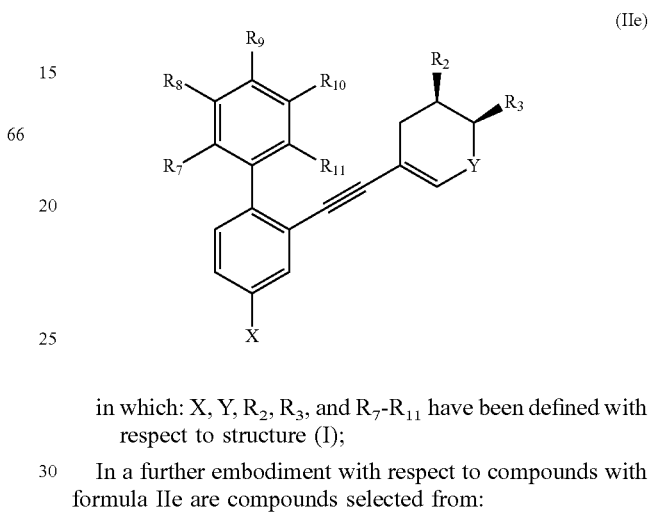

having structure (20) in presence of concentrated hydrochloric acid results into compounds having structure (70); reacting compounds having structure (70) with compounds having structure (24) in presence of palladium and copper catalysts results into compounds having structure (71); reacting compounds having structure (71) with compound having structure (72) results into compounds having formula IId (FIG. 10).

In a further embodiment are compounds of formula (IIe):

in which: X, Y, $R_2$, $R_3$, and $R_7$-$R_{11}$ have been defined with respect to structure (I);

In a further embodiment with respect to compounds with formula IIe are compounds selected from:

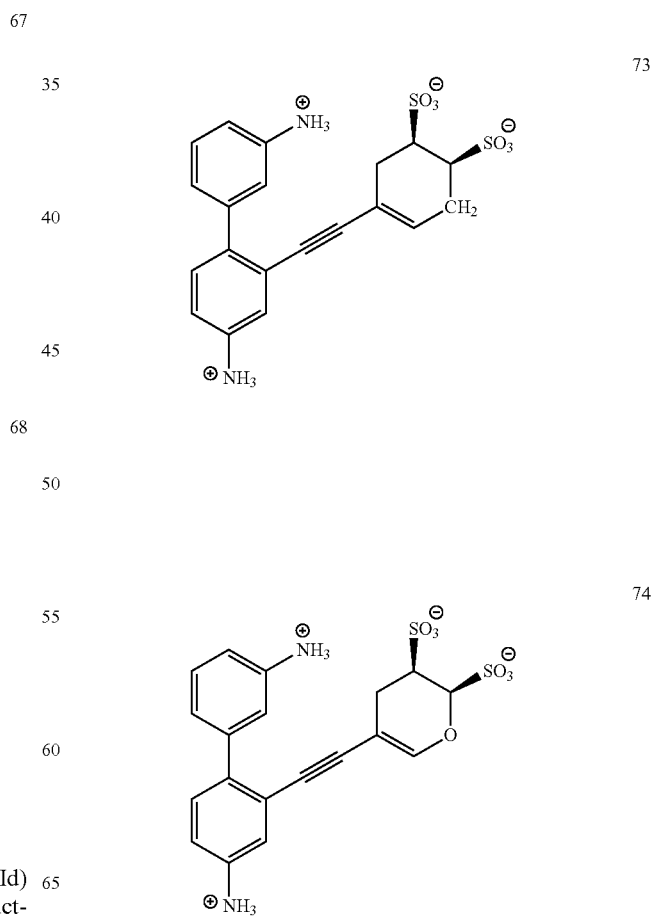

In some embodiments, the compounds with structure (IId) may synthesized according to the following sequence: reacting compounds having structure (69) and a dicyandiamide -continued

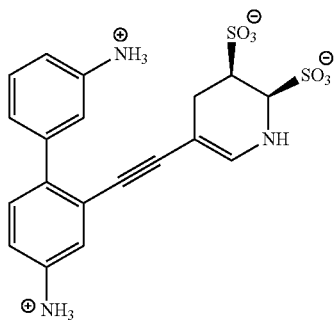

75

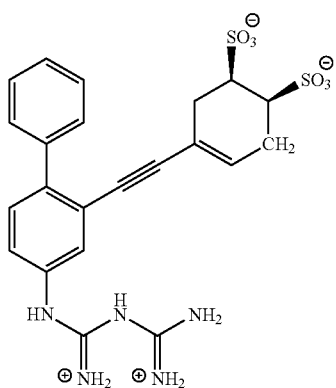

76

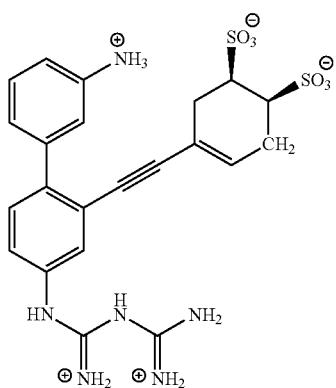

77

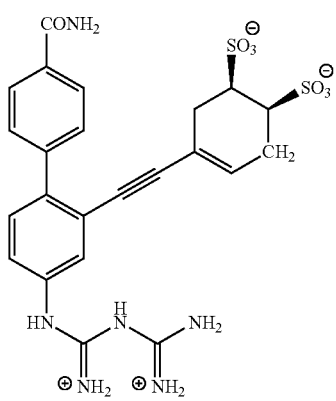

78

Figure 11:
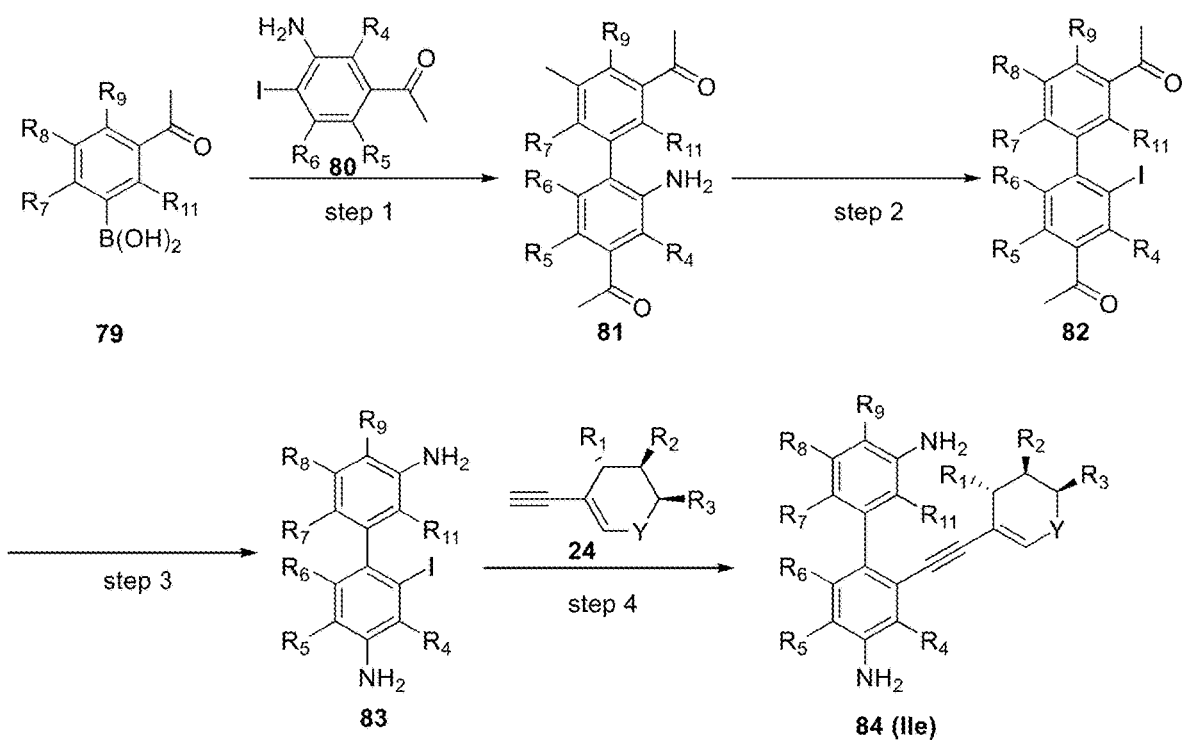
FIG. 11. Synthetic strategy to access compounds of structure IIe.

In some embodiments, the compounds with structure (IIe) may synthesized according to the following sequence: reacting arylboronic acids having structure (79) and aryl iodides having structure (80) in presence of palladium catalysts results into compounds having structure (81); reacting compounds having structure (81) with $HNO_2$ or $NaNO_2$ under acidic conditions gives diazonium salt which upon reaction with copper iodide (CuI) gives compound having structure (82); reacting compounds having structure (82) with hydroxylamine followed by Beckmann rearrangement results into compounds having structure (83); reacting compound have structure (83) with compounds having structure (24) followed by acid or base hydrolysis results into compounds having formula IIe (84) (FIG. 11).

In a further embodiment with respect to structure I, are the compounds of formula III:

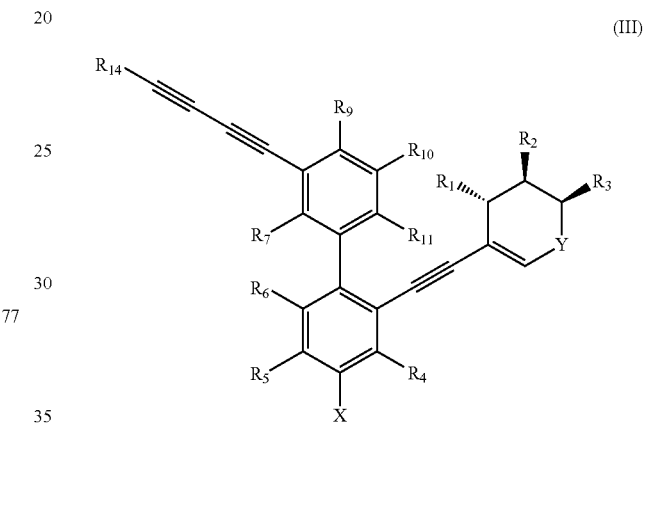

(III)

in which: X, Y, $R_1$, $R_2$, $R_3$, and $R_7$-$R_{11}$ have been defined with respect to structure (I); $R_{14}$ is selected from group consisting of amide and sulfonamide.

In a further embodiment are the compounds of formula IIIa and IIIb:

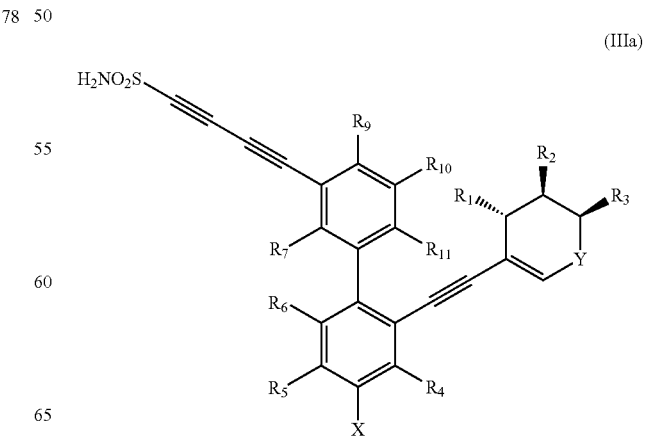

(IIIa)

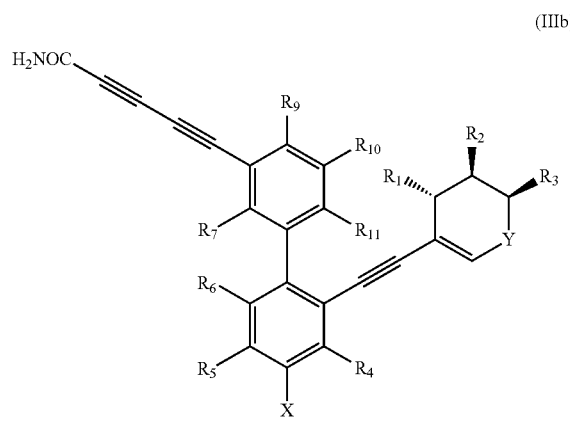
(IIIb)
in which: X, Y, $R_1$, $R_2$, $R_3$, and $R_7$-$R_{11}$ have been defined with respect to structure (I);
In a further embodiment are compounds of formula IIIad:
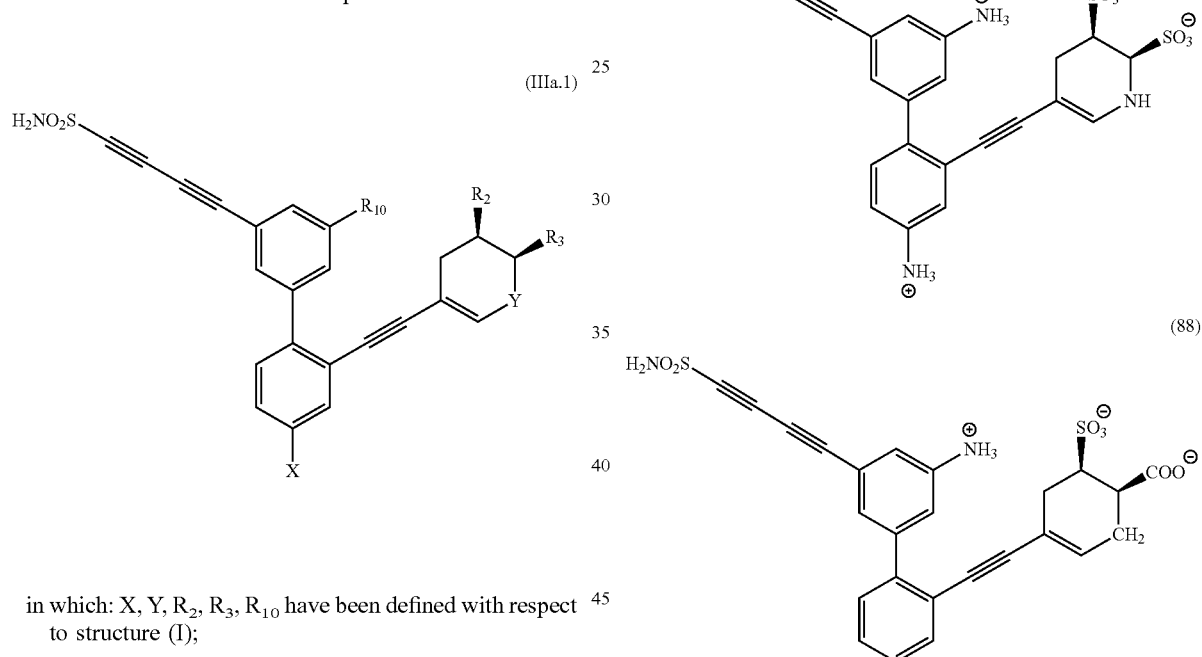
(IIIa.1)
in which: X, Y, $R_2$, $R_3$, $R_{10}$ have been defined with respect to structure (I);
In a further embodiment are compounds selected from:
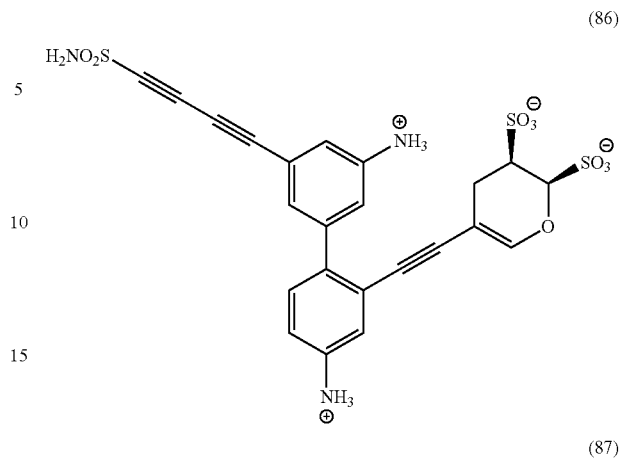
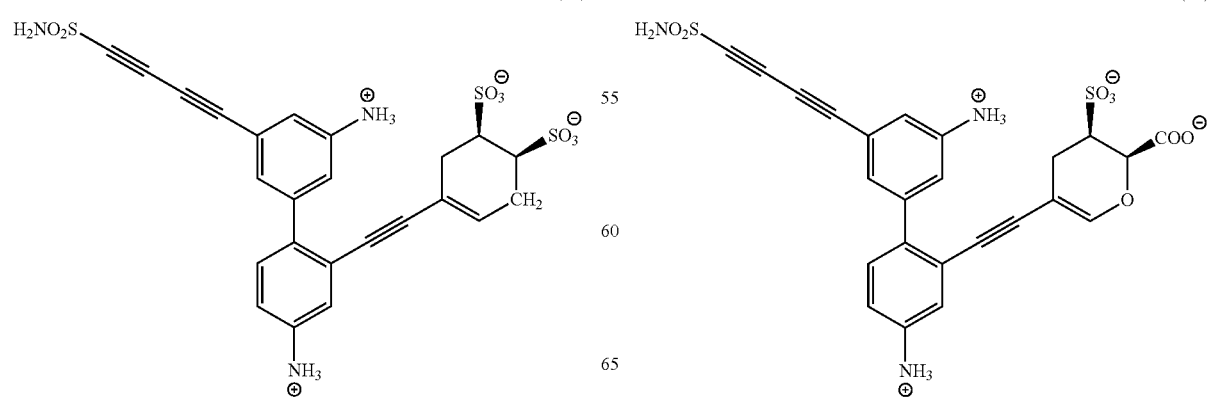

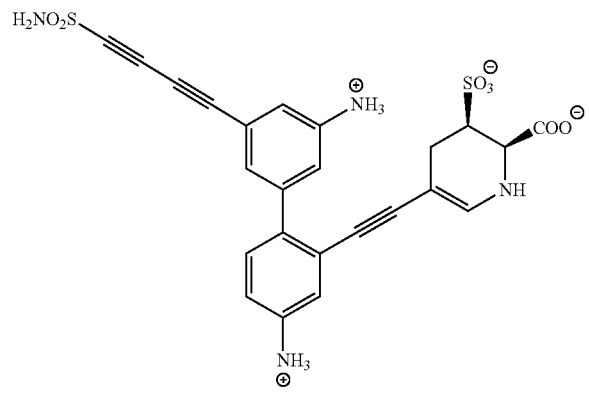
(90)

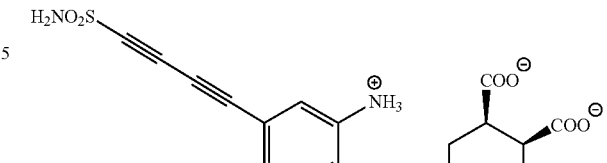
(94)

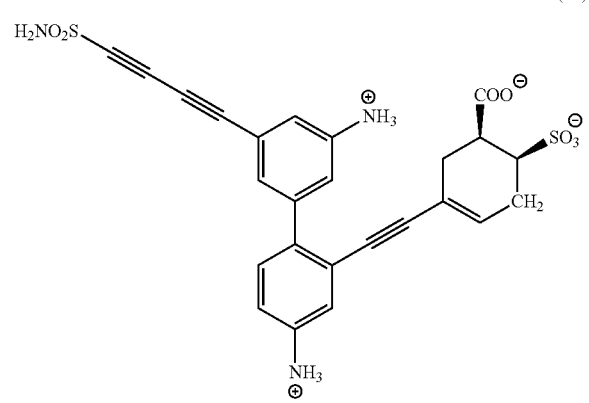
(91)

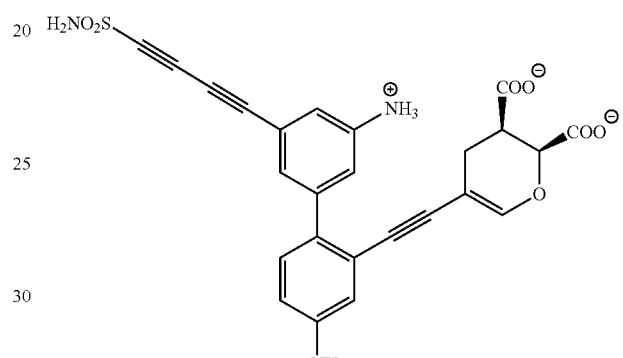
(95)

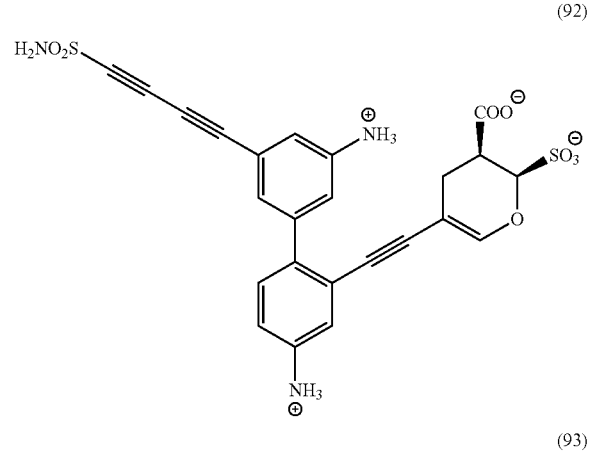
(92)

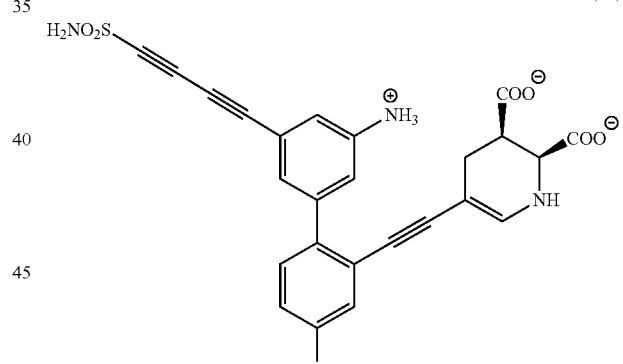
(96)

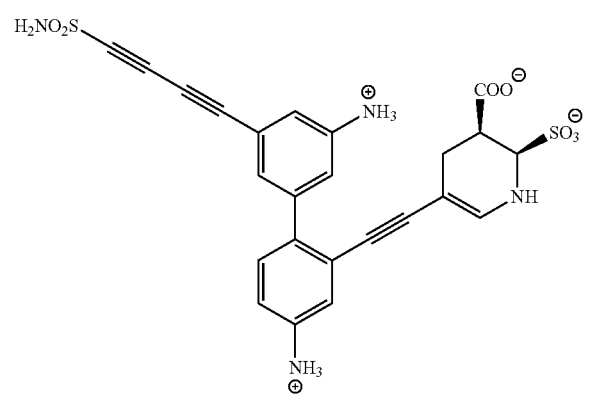
(93)

Figure 12:
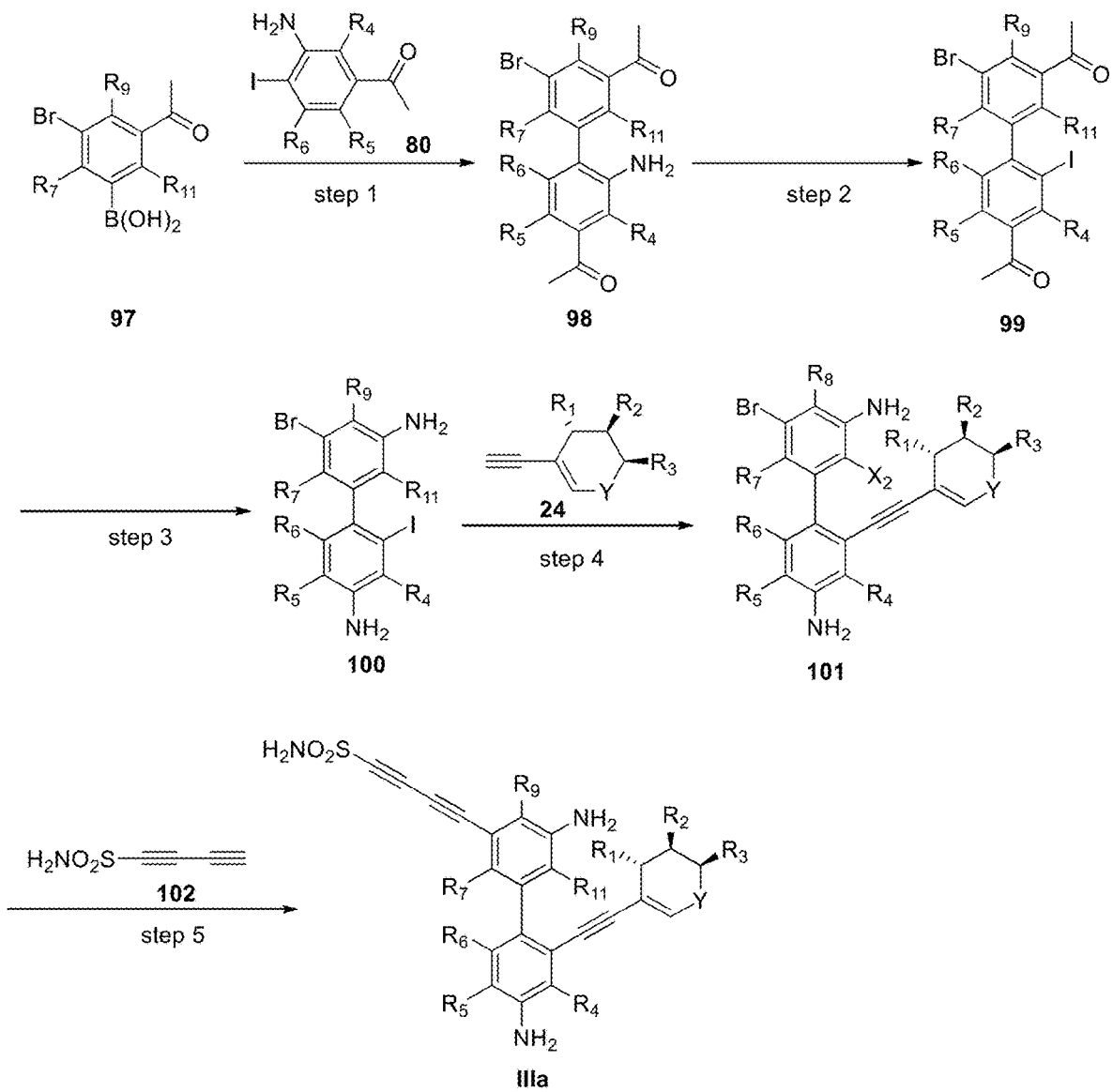
FIG. 12. Synthetic strategy to access compounds of structure IIIa.

In some embodiments, the compounds with structure (IIIa) may synthesized according to the following sequence: reacting arylboronic acids having structure (97) and arylhalides having structure (80) in presence of palladium catalyst gives compounds having structure (98); reacting compounds having structure (98) with $HNO_2$ or $NaNO_2$ under acidic conditions followed by reacting the resulting diazonium salt with copper iodide (CuI) gives compounds having structure (99); reacting compounds having structure (99) with hydroxylamine followed by the Beckmann rearrangement under acidic conditions results into compounds having structure (100); reacting compound have structure (100) with compounds having structure (24) in presence of palladium and copper iodide catalysts results into compounds having structure (101); reacting compounds having structure (101) with compounds having structure (102) in presence of palladium and copper catalysts results into compounds having formula IIIa (FIG. 12).
In a further embodiment with respect to structure IIIb are compounds of formula IIIb.1:
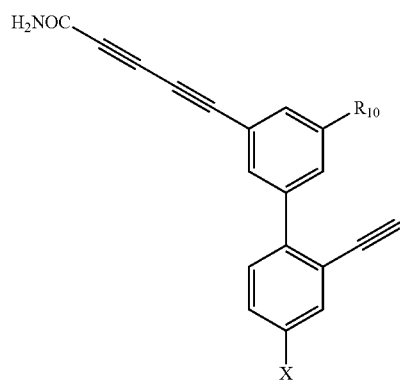
(IIIb.1)
in which: X, Y, $R_2$, $R_3$, $R_{10}$ have been defined with respect to structure (I);
In a further embodiment are compounds selected from:
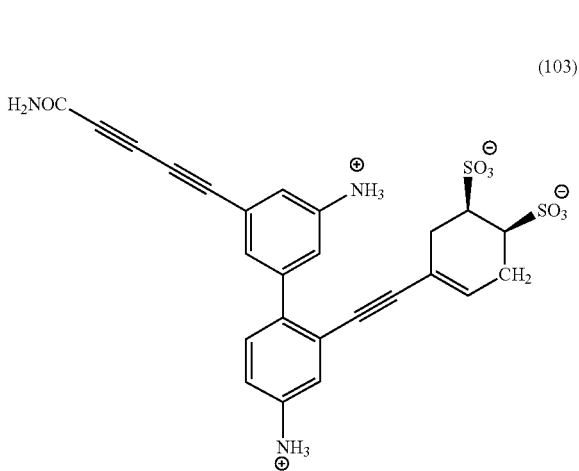
(103)
(104)
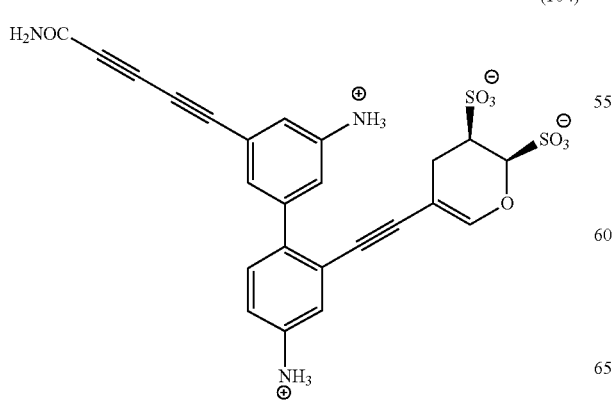
-continued
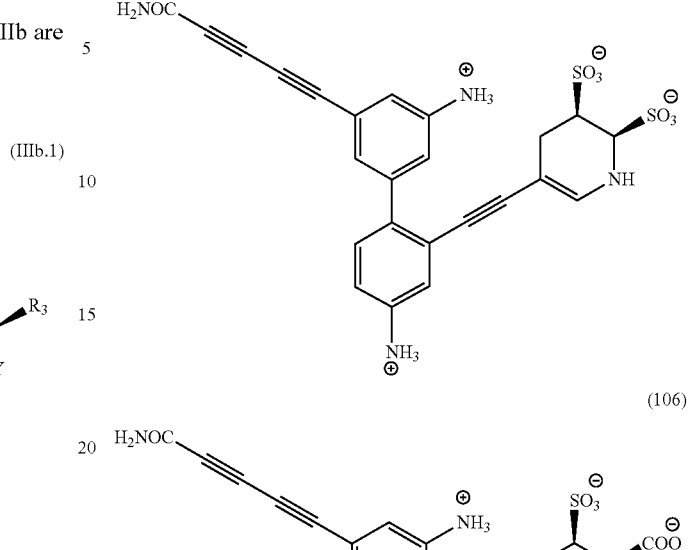
(105)
(106)
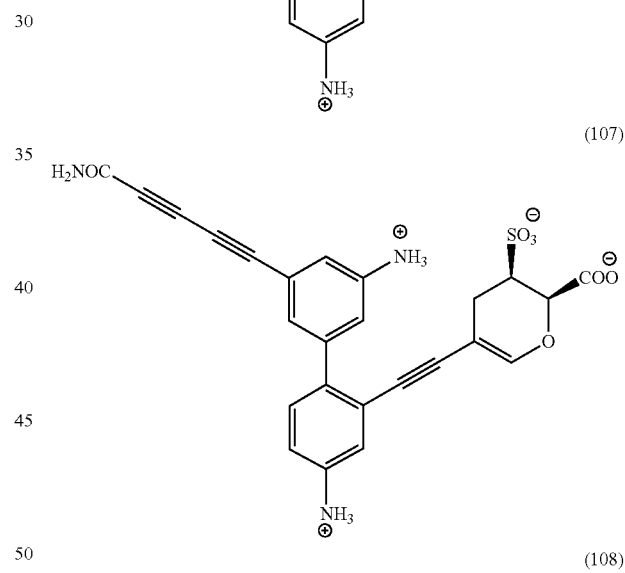
(107)
(108)
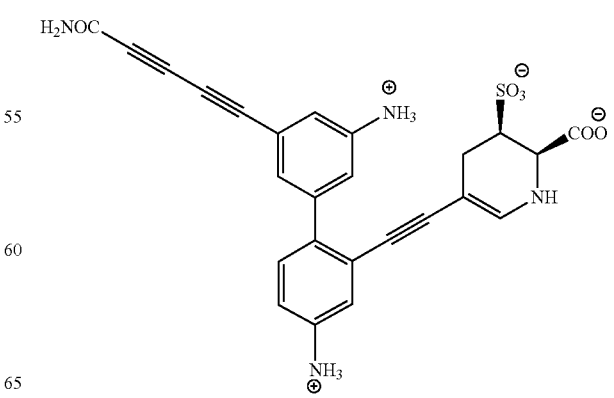

Figure 13:
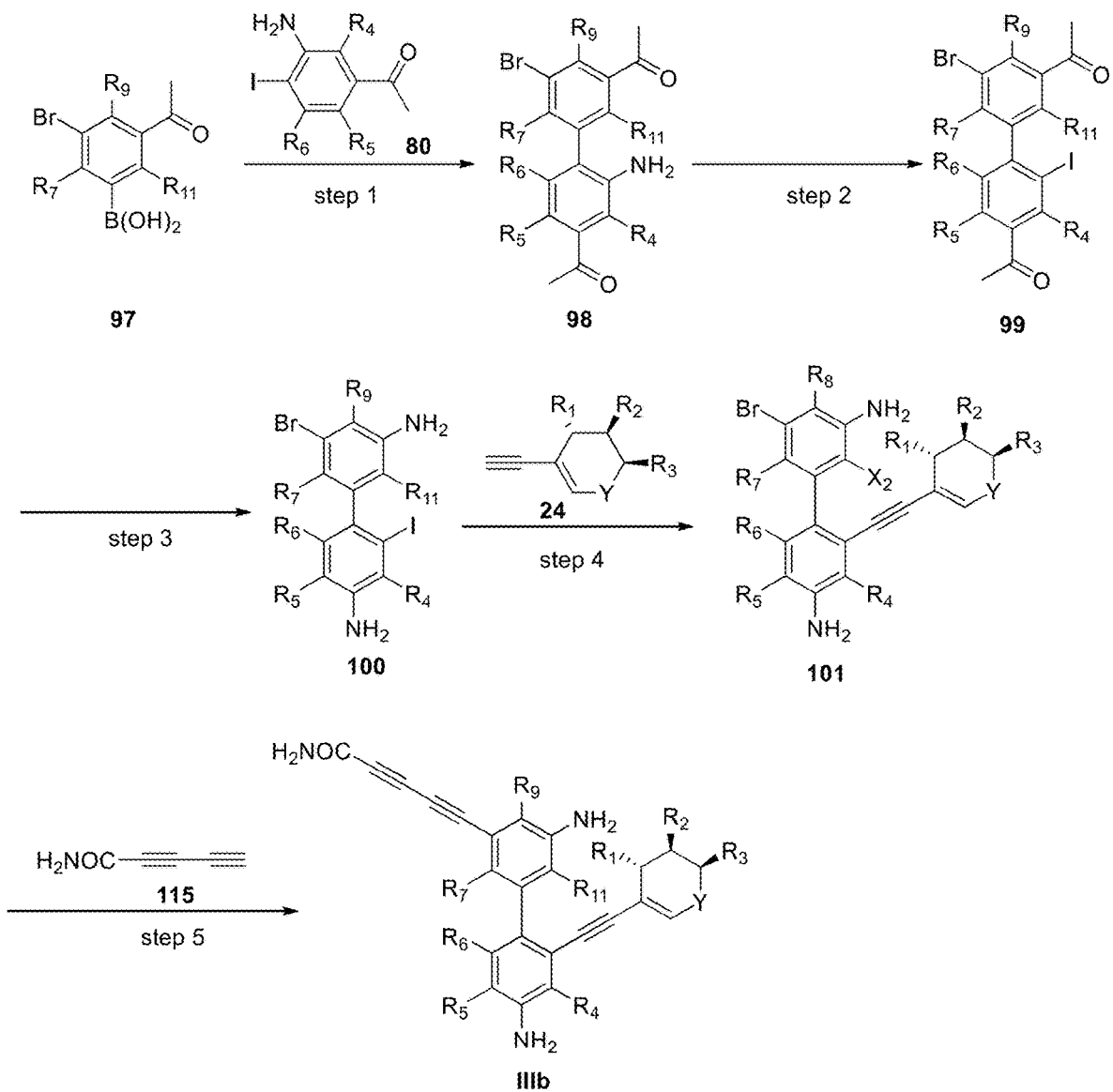
FIG. 13. Synthetic strategy to access compounds of structure IIIb.

In some embodiments, the compounds with structure (IIIa.1) may synthesized according to the following sequence: reacting arylboronic acids having structure (97) and arylhalides having structure (80) in presence of palladium catalyst gives compounds having structure (98); reacting compounds having structure (98) with $HNO_2$ or $NaNO_2$ under acidic conditions followed by reacting the resulting diazonium salt with copper iodide (CuI) gives compounds having structure (99); reacting compounds having structure (99) with hydroxylamine followed by the Beckmann rearrangement under acidic conditions results into compounds having structure (100); reacting compound have structure (100) with compounds having structure (24) in presence of palladium and copper iodide catalysts results into compounds having structure (101); reacting compounds having structure (101) with compounds having structure (115) in presence of palladium and copper catalysts results into compounds having formula IIIb (FIG. 13).

EXAMPLES

The docking studies of following non-limiting examples are provided in Table 1 to further illustrate the utility of the present invention.

| Compound Number | Binding Free Energy | Binding constant (Ki) | Binding site of S1-Domain of SARS-COV-2 Receptor Binding Domain (RBD) |
|---|---|---|---|
| 1 | −14.40 kcal/mol | 32.34 pM | LYS417, ASP 420, TYR421, TYR 453, ASP467, TYR 489, PRO 491, GLN493 |
| 2 | −14.22 kcal/mol | 37.47 pM | LYS417, ASP 420, TYR421, TYR 453, ARG 454, ASP467, TYR 489, PRO 491, GLN493 |
| 3 | −14.04 kcal/mol | 50.77 pM | LYS417, TYR421, TYR 453, ARG 454 ASP467, TYR 489, PRO 491, GLN493 |
| 4 | −13.61 kcal/mol | 110 pM | LYS417, TYR421, TYR 453, ARG 454 ASP467, TYR 489, PRO 491, GLN493 |
| 5 | −13.24 kcal/mol | 200 pM | LYS417, TYR421, TYR 453, ARG 454 ASP467, TYR 489, PRO 491, GLN493 |
| 6 | −13.01 kcal/mol | 290 pM | LYS417, TYR421, TYR 453, ARG 454 ASP467, TYR 489, PRO 491, GLN493 |
| 7 | −13.09 kcal/mol | 250 pM | LYS417, TYR421, TYR 453, ARG 454 ASP467, TYR 489, PRO 491, GLN493 |
| 8 | −13.56 kcal/mol | 120 pM | LYS417, TYR421, TYR 453, ARG 454 ASP467, TYR 489, PRO 491, GLN493 |
| 9 | −13.51 kcal/mol | 130 pM | LYS417, TYR421, TYR 453, ARG 454 ASP467, TYR 489, PRO 491, GLN493 |
| 10 | −11.76 kcal/mol | 2.39 nM | LYS417, TYR421, TYR 453, ARG 454 ASP467, TYR 489, PRO 491, GLN493 |
| 11 | −12.77 kcal/mol | 0.43 nM | LYS417, TYR421, TYR 453, ARG 454 ASP467, TYR 489, PRO 491, GLN493 |
| 12 | −12.52 kcal/mol | 0.66 nM | LYS417, TYR421, TYR 453, ARG 454 ASP467, TYR 489, PRO 491, GLN493 |
| 13 | −13.10 kcal/mol | 250 pM | LYS417, TYR421, TYR 453, ARG 454 ASP467, TYR 489, PRO 491, GLN493 |
| 14 | −13.15 kcal/mol | 230 pM | LYS417, TYR421, TYR 453, ARG 454 ASP467, TYR 489, PRO 491, GLN493 |
| 15 | −12.93 kcal/mol | 0.33 nM | LYS417, TYR421, TYR 453, ARG 454 ASP467, TYR 489, PRO 491, GLN493 |
| 16 | −13.23 kcal/mol | 200 pM | LYS417, TYR421, TYR 453, ARG 454 ASP467, TYR 489, PRO 491, GLN493 |
| 17 | −13.34 kcal/mol | 170 pM | LYS417, TYR421, TYR 453, ARG 454 ASP467, TYR 489, PRO 491, GLN493 |
| 18 | −13.27 kcal/mol | 190 pM | LYS417, TYR421, TYR 453, ARG 454 ASP467, TYR 489, PRO 491, GLN493 |
| 39 | −14.31 kcal/mol | 32.34 pM | LYS417, TYR421, TYR 453, ARG 454 ASP467, TYR 489, PRO 491, GLN493 |
| 40 | −13.42 kcal/mol | 150 pM | LYS417, TYR421, TYR 453, ARG 454 ASP467, TYR 489, PRO 491, GLN493 |
| 41 | −13.33 kcal/mol | 170 pM | LYS417, TYR421, TYR 453, ARG 454 ASP467, TYR 489, PRO 491, GLN493 |
| 42 | −11.96 kcal/mol | 1.72 nM | LYS417, TYR421, TYR 453, ARG 454 ASP467, TYR 489, PRO 491, GLN493 |
| 43 | −11.76 kcal/mol | 2.39 nM | LYS417, TYR421, TYR 453, ARG 454 ASP467, TYR 489, PRO 491, GLN493 |
| 44 | −11.70 kcal/mol | 2.67 nM | LYS417, TYR421, TYR 453, ARG 454 ASP467, TYR 489, PRO 491, GLN493 |
| 51 | −13.28 kcal/mol | 190 pM | LYS417, ASP 420, TYR421, TYR 453, ARG 454 ASP467, TYR 489, PRO 491, GLN493 |
| 52 | −13.70 kcal/mol | 90.20 pM | LYS417, ASP 420, TYR421, TYR 453, ARG 454 ASP467, TYR 489, PRO 491, GLN493 |
| 53 | −13.15 kcal/mol | 230.99 pM | LYS417, ASP 420, TYR421, TYR 453, ARG 454 ASP467, TYR 489, PRO 491, GLN493 |
| 54 | −12.45 kcal/mol | 0.75 nM | LYS417, ASP 420, TYR421, TYR 453, ARG 454 ASP467, TYR 489, PRO 491, GLN493 |
| 55 | −11.56 kcal/mol | 3.37 nM | LYS417, ASP 420, TYR421, TYR 453, ARG 454 ASP467, TYR 489, PRO 491, GLN493 |
| 56 | −11.13 kcal/mol | 6.97 nM | LYS417, ASP 420, TYR421, TYR 453, ARG 454 ASP467, TYR 489, PRO 491, GLN493 |
| 63 | −14.23 kcal/mol | 37.05 pM | LYS417, TYR421, TYR 453, ARG 454 ASP467, TYR 489, PRO 491, GLN493 |

-continued

| Compound Number | Binding Free Energy | Binding constant (Ki) | Binding site of S1-Domain of SARS-COV-2 Receptor Binding Domain (RBD) |
|---|---|---|---|
| 64 | −13.14 kcal/mol | 230 pM | LYS417, ASP 420, TYR421, TYR 453, ARG 454 ASP467, TYR 489, PRO 491, GLN493 |
| 65 | −12.86 kcal/mol | 0.38 nM | LYS417, ASP 420, TYR421, TYR 453, ARG 454 ASP467, TYR 489, PRO 491, GLN493 |
| 66 | −11.20 kcal/mol | 6.12 nM | LYS417, ASP 420, TYR421, TYR 453, ARG 454 ASP467, TYR 489, PRO 491, GLN493 |
| 67 | −11.07 kcal/mol | 7.65 nM | LYS417, ASP 420, TYR421, TYR 453, ARG 454 ASP467, TYR 489, PRO 491, GLN493 |
| 68 | −11.27 kcal/mol | 5.45 nM | LYS417, ASP 420, TYR421, TYR 453, ARG 454, ASP467, TYR 489, PRO 491, GLN493 |
| 73 | −11.46 kcal/mol | 3.97 nM | LYS417, TYR421, TYR 453, ARG 454, ASP467, TYR 489, GLN493 |
| 74 | −11.76 kcal/mol | 2.42 nM | LYS417, TYR421, TYR 453, ARG 454, ASP467, PRO 491, GLN493 |
| 75 | −11.49 kcal/mol | 3.78 nM | LYS417, TYR421, TYR 453, ARG 454, ASP467, PRO 491, GLN493 |
| 76 | −14.30 kcal/mol | 32.82 pM | LYS417, ASP 420, TYR421, TYR 453, ARG 454, ASP467, TYR 489, PRO 491, GLN493 |
| 77 | −13.34 kcal/mol | 170 pM | LYS417, ASP 420, TYR421, TYR 453, ARG 454, ASP467, TYR 489, PRO 491, GLN493 |
| 78 | −14.35 kcal/mol | 30.49 pM | LYS417, ASP 420, TYR421, TYR 453, ASP467, TYR 489, PRO 491, GLN493 |
| 85 | −12.98 kcal/mol | 0.30 nM | LYS417, TYR421, TYR 453, ARG 454, ASP467, TYR 489, PRO 491, GLN493 |
| 86 | −13.35 kcal/mol | 160 pM | LYS417, TYR421, TYR 453, ARG 454, ASP467, TYR 489, PRO 491, GLN493 |
| 87 | −13.23 kcal/mol | 200 pM | LYS417, TYR421, TYR 453, ARG 454, ASP467, TYR 489, PRO 491, GLN493 |
| 88 | −12.53 kcal/mol | 0.65 nM | LYS417, TYR421, TYR 453, ARG 454 ASP467, TYR 489, PRO 491, GLN493 |
| 89 | −12.35 kcal/mol | 0.88 nM | LYS417, TYR421, TYR 453, ARG 454 ASP467, TYR 489, PRO 491, GLN493 |
| 90 | −11.61 kcal/mol | 3.06 nM | LYS417, TYR421, TYR 453, ARG 454 ASP467, TYR 489, PRO 491, GLN493 |
| 91 | −12.87 kcal/mol | 0.37 nM | LYS417, TYR421, TYR 453, ARG 454 ASP467, TYR 489, PRO 491, GLN493 |
| 92 | −13.16 kcal/mol | 230 pM | LYS417, TYR421, TYR 453, ARG 454 ASP467, TYR 489, PRO 491, GLN493 |
| 93 | −12.57 kcal/mol | 0.61 nM | LYS417, TYR421, TYR 453, ARG 454 ASP467, TYR 489, PRO 491, GLN493 |
| 94 | −12.63 kcal/mol | 0.55 nM | LYS417, TYR421, TYR 453, ARG 454 ASP467, TYR 489, PRO 491, GLN493 |
| 95 | −11.92 kcal/mol | 1.83 nM | LYS417, TYR421, TYR 453, ARG 454 ASP467, TYR 489, PRO 491, GLN493 |
| 96 | −12.21 kcal/mol | 1.12 nM | LYS417, TYR421, TYR 453, ARG 454 ASP467, TYR 489, PRO 491, GLN493 |
| 103 | −13.16 kcal/mol | 225.02 pM | LYS417, TYR421, TYR 453, ARG 454 ASP467, TYR 489, PRO 491, GLN493 |
| 104 | −13.01 kcal/mol | 0.29 nM | LYS417, TYR421, TYR 453, ARG 454 ASP467, TYR 489, PRO 491, GLN493 |
| 105 | −12.40 kcal/mol | 0.82 nM | LYS417, TYR421, TYR 453, ARG 454 ASP467, TYR 489, PRO 491, GLN493 |
| 106 | −11.70 kcal/mol | 2.63 nM | LYS417, TYR421, TYR 453, ARG 454 ASP467, TYR 489, PRO 491, GLN493 |
| 107 | −12.25 kcal/mol | 1.04 nM | LYS417, TYR421, TYR 453, ARG 454 ASP467, TYR 489, PRO 491, GLN493 |
| 108 | −11.85 kcal/mol | 2.06 nM | LYS417, TYR421, TYR 453, ARG 454 ASP467, TYR 489, PRO 491, GLN493 |

Binding energies are expressed in kcal/mol. Binding constants are expressed as nanomolar (nM) or picomolar (pM) concentrations.

General Consideration.

In-silico Study: Structure of the SARS-COV-2 ("closed state") PDB ID: 6VXX was obtained from RCSB Protein Data Bank. Docking studies were performed using AutoDock 4.2 provided by the Scripps Research Institute (La Jolla, Calif.). In specific, the Lamarckian genetic algorithm was used to determine the binding free energies ($\Delta G_{binding}=\Delta G_{vdv}+\Delta G_{elec}+\Delta G_{Hbond}+\Delta G_{desolv}+\Delta G_{torsional}$) and binding constants ($K_i$) between the compounds of present invention and the closed conformation of the SARS-COV-2 RBD (receptor binding domain). Single point DFT (density functional theory) calculations were performed between selected molecules of present invention and the closed contact amino-acid residues of the SARS-COV-2 RBD.

General procedure to synthesize compounds having structure 21, 46, 58, and 70: In a 5 mL microwave reactor, a solution of amine (19, 45, 57, or 69) (1 equivalent) and dicyandiamide (20) (1 equivalent) is prepared in acetonitrile (0.5M). Next, a 2N solution of trimethylsilylchloride (TMSCl) (1 equivalent) is slowly added to the stirred solution of the reaction mixture. The resulting mixture is subjected to the microwave radiation before cooling down to 50° C. At this stage, 3 equivalents of isopropyl alcohol are added, and the reaction mixture is again subjected to the microwave radiation. Upon cooling, compound 21, 46, 58, or 70 should precipitate as biguanidinium hydrochloride salt. This salt can be dried in vacuo and can be converted to free amine under basic conditions. For non-limiting representative procedures see: (a) Mayer, S.; Daigle, D. M.; Brown, E. D.; Khatri, J.; Organ, M. G. *J. Comb. Chem.* 2004, 6, 776-782; (b) Sun, Y.; Gu, J.; Wang, H.; Sessler, J. L.; Thordarson, P.; Lin, Y-J.; Gong, H. *J. Am. Chem. Soc.* 2019, 141, 20146-20154; and (c) Shapiro, S. L.; Parrino, V. A.; Freedman, L. *J. Am. Chem. Soc.* 1959, 81, 4635-4639.

General procedure of Suzuki coupling to synthesize compounds having structure 23, 48, 60, 81, and 98: A mixture of aryl iodide having structure 21, 46, 58, 79 or 97 (1.0 equivalent) and aryl boronic acid derivatives having structure 22, 47, 59, or 80 (1.2 equivalent) are dissolved in dioxane (0.05M) and water (3.0 mL) under inert atmosphere. The solution should then be degassed by bubbling Argon or $N_2$ gas through the mixture for approximately 15 minutes before adding tetrakis(triphenyl-phosphine) palladium (0) (5 mol %) and potassium carbonate (2.5 equivalents). The reaction mixture should then be stirred at 80° C. until the TLC shows consumption of reactants. Next, the reaction mixture should be cooled to room temperature and diluted with ethyl acetate, washed with water. The combined organic layers should be dried over anhydrous $Na_2SO_4$ or $MgSO_4$ and the solvent should be removed under vacuum. The crude product can be purified using silica gel column chromatography. For non-limiting representative procedures see: (a) Li, W.; Xiao, G.; Deng, G.; Liang, L. *Org. Chem. Front.*, 2018, 5, 1488-1492; (b) Xu, Y.; Liu, X.; Chen, W.; Deng. G.; Liang, Y. *Org. Chem.* 2018, 83, 22, 13930-13939; (c) Wei, B.; Zhang, D.; Chen, Y-H.; Lei, A.; Knochel, P. *Angew Chem Int Ed Engl.* 2019, 58, 15631-15635; (d) Larpent, P.; Jouaiti, A.; Kyritsakasa, N.; Hosseini, M. W. *Chem. Commun.*, 2019, 55, 91-94; and (e) Blair, A.; Stevenson, L.; Dewar, D.; Pimlottc, S. L.; Sutherland, A. *Med Chem. Commun.*, 2013, 4, 1461-1466.

General procedure of Sonogashira coupling to synthesize compounds having structure 25, 29, 49, 61, 71, 84, and 101: A 10 mL 1:1 v/v mixture of tetrahydrofuran (THF) and triethylamine is degassed for 15 minutes by bubbling argon gas in a round bottom flask. To this solution, 1 mmol of compound having structure 24 and 1 mmol of compound having structure 23, 27, 48, 60, 70, 83, or 100 are added followed by addition of 5 mol % of bis(triphenylphosphine) palladium(II) dichloride $(Pd(PPh_3)_2Cl_2)$ and 5 mol % copper (I) iodide (CuI). The mixture is refluxed under inert atmosphere until the TLC shows consumption of reactants. Next, the solvents are removed under reduced pressure on rotary evaporator before adding dichloromethane $(CH_2Cl_2)$. The organic phase should be washed with brine and extracted dichloromethane, dried over anhydrous MgSO4 and filtered. The solvent should be removed again before purifying the crude product using silica gel column chromatography. For non-limiting representative procedures see: (a) Peressin, N.; Adamski, M.; Schibli, E. M.; Ye, E.; Frisken, B. J.; Holdcroft, S. Macromolecules 2020, 53, 3119-3138; (b) Rami, F.; Bächtle, F.; Plietker, B. *Catal. Sci. Technol.*, 2020, 10, 1492-1497; (c) Chen, Y-Y.; Wang, H.; Zhang, D. W.; Hou, J-L.; Li, Z-T. *Chem. Commun.*, 2015, 51, 12088-12091; and (d) Burnett, J. C.; Lim, C.; Peyser, B. D.; Samankumara, L. P.; Kovaliov, M; Colombo, R.; Bulfer, S. L.; LaPorte, M. G.; Hermone, A. R.; McGrath, C. F.; Arkin, M. R.; Gussio, R.; Huryn, D. M.; Wipf, P. *Org. Biomol. Chem.*, 2017, 15, 4096-4114.

General procedure of Sonogashira coupling to synthesize compounds having structure 24: To a solution of 0.15 M solution of TMS-alkyne having structure 29 (1 equivalent) in methanol is added potassium carbonate (0.2 equivalent) and the reaction mixture is stirred at room temperature under inert atmosphere ($N_2$ or Argon) until TLC shows consumption of TMS-alkyne 29. The reaction mixture should then be concentrated in vacuo, diluted with diethyl ether and washed with water, brine and must be dried over $MgSO_4$ or $Na_2SO_4$. Purification of 24 can be performed by flash chromatography using petroleum ether and ether as eluting solvents. For non-limiting representative procedures see: Paoletta, S.; Tosh, D. K.; Finley, a.; Gizewski, E. T.; Moss, S. M.; Gao, Z-G.; Auchampach, J. A.; Salvemini, D.; Jacobson, K. A. *J. Med. Chem.* 2013, 56, 5949-5963; (b) McDermott, T. S.; Bhagavatula, L.; Borchardt, T. B.; Engstrom, K. M.; Gandarilla, J.; Kotecki, B. J.; Kruger, A. W.; Rozema, M. J.; Sheikh, A. Y.; Wagaw, S. H.; Wittenberger, S. *J. Org. Process Res. Dev.* 2009, 13, 1145-1155.

General procedure of Diels-Alder reaction to synthesize compounds having structure 27a, 27b and 27c: To a solution of 0.05M solution of compound having structure 31, 35, or 38 (1 mmol) in dry xylenes is added a compound having structure 30 (1.2 mmol) and the reaction mixture is refluxed until the TLC shows consumption of the reactants. Subsequently, the crude Diels-Alder product can be isolated by removing solvent under vacuo. Further purification using silica gel column chromatography can provide the desired product. For non-limiting representative procedures see: (a) Hopf, H.; Theurig, M. *Angew Chem.* 1994, 106, 1173-1174; (b) Feng, H-X.; Wang, Y-Y.; Chen, J.; Zhou, L. *Adv. Synth. Catal.* 2015, 357, 940-944; (c) Hall, H. K.; Nogues, P.; Rhoades, J. W.; Sentman, R. C.; Detar, M. *J. Org. Chem.* 1982, 47, 1451-1455. (d) Erfurt, K.; Wandzik, I.; Walczak, K.; Matuszek, K.; Chrobok, A. *Green Chem.*, 2014, 16, 3508-3514; (e) Brown, P. A.; Bonnert, R. V.; Jenkins, P. R.; Selim, M. R. *Tetrahedron Lett.* 1987, 28, 693-696; (f) Jiang, H.; He, L.; Li, X.; Chen, H.; Wua, W.; Fua, W. *Chem. Commun.*, 2013, 49, 9218-9220; (g) Afarinkia, K.; Daly, N. T.; Gomez-Farnos, S.; Joshi, S. *Tetrahedron. Lett.* 1997, 38, 2369-2372; (h) Afarinkia, K.; Bearpark, M. J.; Ndibwami, A. *J. Org. Chem.* 2005, 70, 1122-1133; and (i) Carothers, W. H.; Collins, A. M.; Kirby, J. E. *J. Am. Chem. Soc.* 1933, 55, 786-788.

General procedure of alkylation to synthesize compounds having structure 35 and 38: To a 0.8M solution of bis-acid chloride having structure 33 or 37 (1 equivalent) and a trifluoromethyl benzyl alcohol having structure 34 (2 equivalents) in dicholromethane $(CH_2Cl_2)$ is added dropwise a 2M solution of (1,4-diazabicyclo[2.2.2]octane) (2.5 equiv) in dicholromethane $(CH_2Cl_2)$. The resulting solution is stirred at room temperature until the TLC shows consumption of reactants. The reaction is then be quenched by adding 1 M NaOH (1 mL). Next, the resulting solution should be diluted with ethyl acetate and washed with saturated $NaHCO_3$, 0.1 M HCl, water, and brine. Separating and drying the organic phase over $Na_2SO_4$ followed by removing the solvent using rotary evaporator should give the crude product. The crude product may be used directly for the next step or may be purified using column chromatography. For non-limiting representative procedures see: (a) Pauff, S. M.; Miller, S. C. *J. Org. Chem.* 2013, 78, 711-716; and (b) Behroz, I.; Durkin, P.; Gratz, S.; Seidel, M.; Rostock, L.; Spinczyk, M.; Weston, J. B.; Süssmuth, R. D. *Chem. Eur. J.* 2019, 25, 16538-16543.

General procedure to synthesize compounds having structure 33 and 37: The bischlorination of disulfonic, dicarboxylic and mixed acid can be performed by treating compounds having structure 32 or 36 (1 mmol) with freshly distilled thionyl chloride (5 mL) in presence of a catalytic amount of DMF (25 µL) under inert argon (Ar) or nitrogen ($N_2$) atmosphere. The product can be obtained by filtration and azeotropic distillation with toluene. For non-limiting representative procedures see: (a) Hendrickson, J. B. *J. Am. Chem. Soc.* 1962, 84, 653-659; (b) Alsibai, W.; Hahnenkamp, A.; Eisenblatter, M.; Riemann, Schafers, M.; Bremer, C.; Haufe, G.; ⊥, Höltke, C. *J. Med. Chem.* 2014, 57, 9971-9982; (c) Kheirabadi, M.; Creech, G. S.; Qiao, J. X.; Nirschl, D. S.; Leahy, D. K.; Boy, K. M.; Carter, P. H.; Eastgate, M. D. *J. Org. Chem.* 2018, 83, 4323-4335; and (d) McGeary, R. P.; Bennett, A. J.; Tran, Q. B.; Prins, J.; Ross, B. P. *Tetrahedron* 2009, 65, 3990-3997.

General procedure of alkylation to synthesize compounds having structure IIa, IIb, and IIc: A solution of 2 equivalents of alkyl halide having structure 25, 49 or 61 and 1 equivalent of pyridine derivative having structure 26, 50, or 62 in 0.5 M acetone is stirred until the TLC show the consumption of reactants. The resulting solid should be washed with ethyl acetate and the solvent should be removed using a rotary evaporator. The resulting salt is treated with aqueous sodium carbonate followed by addition of hydrochloric acid to give zwitterionic IIa, IIb or IIc. For non-limiting representative procedures see: (a) Bures, F.; Cvejn, D.; Melánová, K.; Benesš, L.; Svoboda, J.; Zima, V.; Pytela, O.; Mikysek, T.; Růšičková, Z.; Kityk, I. V.; Wojciechowskif, A.; AlZayed, N. *J. Mater. Chem. C*, 2016, 4, 468-478; (b) Rotering, P.; Wilm, L. F. B.; Werra, J. A.; Dielmann, F. *Chem. Eur. J.* 2020, 26, 406-411; (c) Baggi, G.; Boiocchi, M.; Fabbrizzi, L.; Mosca, L. *Chem. Eur. J.* 2011, 17, 9423-9439; (d) Chien, C. H.; Leung, M-K.; Su, J-K.; Li, G-H.; Liu, Y-H.; Wang, Y. *J. Org. Chem.* 2004, 69, 1866-1871; (d) Binderup, E.; Bjorkling, F.; Hjarnaa P. V.; Latini, S.; Baltzer, B.; Carlsen, M.; Binderup, L. *Bioorg Med Chem Lett.* 2005, 15, 2491-2494; (e) Sassoon, R. E.; Aizenshtat, Z.; Rabani, J. *J. Phys. Chem.* 1985, 89, 1182-1190; (f) Lethesh, K. C.; Evjen, S.; Raj, J. J.; Roux, D. C. D.; Venkatraman, V.; Jayasayee, K.; Fiksdahl, A. *Front. Chem.* 2019, 7, 625; (g) Febriansyah, B.; Neo, C. S. D.; Giovanni, D.; Srivastava, S.; Lekina, Y.; Koh, T. M.; Li, Y.; Shen, Z. X.; Asta, M.; Sum, T. C.; Mathews, N.; England, J. *Chem. Mater.* 2020, 32, 4431-4441; (h) Gooseman, N. E. J.; O'Hagan, D.; Peach, M. J. G.; Slawin, A M. Z.; Tozer, D. J.; Young, R. J. *Angew. Chem. Int. Ed.* 2007, 46, 5904-5908; and (i) Kay, A. J.; Woolhouse, A. D.; Gainsford, G. J.; Haskell, T. G.; Wyss, C. P.; Giffin, S. M.; McKinnieb, I. T.; Barnes, T. H. *J. Mater. Chem.,* 2001, 11, 2271-2281.

General procedure to synthesize compounds having structure 82 and 99: To cold stirred solution (0° C.) of XX (1 mmol) in deionized water/HCl (20 mL, 1:1 v:v) is added dropwise a cold solution of sodium nitrite (6 mmol) in deionized water (6 mL) over a span of 2 hours. The reaction mixture is stirred at 0° C. for another 1-hour min and slowly poured into a solution of potassium iodide (60 mmol) in deionized water (12 mL). The resulting reaction mixture is stirred at 60° C. until TLC shows consumption of reactants. Next, the reaction is quenched by adding sodium hydrogen sulfite in portions followed by washing with water and extracting with dichloromethane. The organic phases are combined and dried over $Na_2SO_4$ before removing solvent on the rotary evaporator. Crude product can be purified using column chromatography using pretreated silica gel or neutral alumina. For non-limiting representative procedures see: (a) Tahmouresilerd, B.; Moody, M.; Agogo, L.; Cozzolino, A. F. Dalton Trans., 2019, 48, 6445-6454; (b) Luo, T. Y.; Liu, C.; Gan, X. Y.; Muldoon, P. F.; Diemler, N. A.; Millstone, J. E.; Rosi, N. L. J. Am. Chem. Soc. 2019, 141, 2161-2168; (c) Krasnokutskaya, E. A.; Semenischeva, N. I.; Filimonov, V. D.; Knochel, P. Synthesis, 2007, 81-84; and (d) Filimonov, V. D.; Semenischeva, N. I.; Krasnokutskaya, E. A.; Tretyakov, A. N.; Hwang, H. Y.; Chi, K.-W. Synthesis, 2008, 185-187.

General procedure of Beckmann rearrangement to synthesize compounds having structure 83 and 100: Beckmann rearrangement A solution of compounds having structure 82 or 99 (1.0 mmol), hydroxylamine hydrochloride (7.0 mmol) and sodium hydroxide (8.0 mmol) is prepared in water (2 mL) and ethanol (12 mL, 100%). The mixture is then gently refluxed with constant stirring until the TLC shows consumption of reactants. The reaction mixture is then allowed attain the room temperature and the solvent is removed using a rotary evaporator followed by addition of water. The suspension is stirred for another 30 minutes and filtered to yield a crude oxime. The oxime (1.0 mmol) is then added to polyphosphoric acid (9 gm) at 100° C. with constant stirrring under inert atmosphere. The reaction mixture is heated until the TLC shows consumption of reactants. Next, the reaction mixture is neutralized in a ice bath using 10% aqueous sodium hydroxide followed by washing with water until the washings tested neutral. Free amine can be extracted using solvent extraction. For non-limiting representative procedures see: (a) Kalgutkar, R. S.; Lahti, P. M. *Tetrahedron Lett.* 2003, 44, 2625-2628; (b) Yadav, L. D. S.; Patel, R.; Srivastava, V. P. Synthesis, 2010, 1771-1776; and (c) Ranin, R. S.; Bosson, J.; Diez-Gonzalez, S.; Marion, N.; Nolan, S. P. *J. Org. Chem.,* 2010, 75, 1197-1202.

General procedure of Beckmann rearrangement to synthesize compounds having structure IId: A mixture of Zincke salt (2,4-Dinitrophenyl)pyridinium chloride having structure 71 (5 mmol) and amine having structure 72 (1 mmol) in ethanol (6 mL) is refluxed until TLC shows consumption of amine. Next, the reaction mixture is filtered and washed with acetone. The resulting pyridinium salt can be recrystallized from $CH_3OH$/THF. For non-limiting representative procedures see: a) Zhan, T-G.; Zhou, T. Y.; Lin, F.; Zhang, L.; Zhou, C.; Qi, Q. Y.; Li, Z-T.; Zhao, X. *Org. Chem. Front.,* 2016, 3, 1635-1645; (b) Nanasawa, M.; Miwa, M.; Hirai, M.; Kuwabara, T. *J. Org. Chem.,* 2000, 65, 593-595;

General procedure of Cadiot-Chodkiewicz coupling to synthesize compounds having structure 102: To a solution of 70% ethylamine aqueous solution (1 mL), 0.5 mL of distilled water, hydroxylamine hydrochloride (0.1 g), and copper(I) chloride (0.02 g) in a 25 mL round bottom flask under inert atmosphere is dropwise added ethynesulfonic acid (1 mmol) in 3 mL of THF over the period of 10 min followed by addition of (iodoethynyl)trimethylsilane in 3 mL of THF over the period of 30 min. The reaction mixture is stirred until TLC shows consumption of reactants. Next, the solvent is removed under reduced pressure followed by addition of aqueous HCl solution (1 mol/L) until the solution is acidic. The resulting solution is then extracted with diethyl ether followed by removing the solvent under reduced pressure. The crude product (1 mmol) is then treated freshly distilled thionyl chloride (5 mL) in presence of a catalytic amount of DMF (25 µL) under inert argon (Ar) or nitrogen ($N_2$) atmosphere. The resulting sulfonyl chloride derivative can be obtained by filtration and azeotropic distillation with toluene. To a stirred solution of sulfonyl chloride derivative (1 mmol) is added aqueous 35% solution of ammonium hydroxide at 0° C. The resulting reaction mixture is stirred at room temperature until the TLC shows consumption of reactants. The reaction mixture is then washed with water, extracted with ethyl acetate and dried over anhydrous $Na_2SO_4$. The solvent is evaporated under reduced pressure on rotary evaporator to give the desired product. Next, the For non-limiting representative procedures see: (a) Hendrickson, J. B. I *Am. Chem. Soc.* 1962, 84, 653-659; (b) Alsibai, W.; Hahnenkamp, A.; Eisenblatter, M.; Riemann, Schafers, M.; Bremer, C.; Haufe, G.; 1, Höltke, C. *J. Med. Chem.* 2014, 57, 9971-9982; (c) Kheirabadi, M.; Creech, G. S.; Qiao, J. X.; Nirschl, D. S.; Leahy, D. K.; Boy, K. M.; Carter, P. H.; Eastgate, M. D. I *Org. Chem.* 2018, 83, 4323-4335; (d) McGeary, R. P.; Bennett, A. J.; Tran, Q. B.; Prins, J.; Ross, B. P. *Tetrahedron* 2009, 65, 3990-3997; and (e) Wang, P.; Luchowska-Stańska, U.; Basten, B. V.; Chen, H.; Liu, Z.; Wiejak, J.; Whelan, P.; Morgan, D.; Lochhead, E.; Barker, G.; Rehmann, H.; Yarwood, S. J.; Zhou, J. *J. Med. Chem.* 2020, 63, 5159-5184.

What is claimed is:
1. A compound of formula (I):

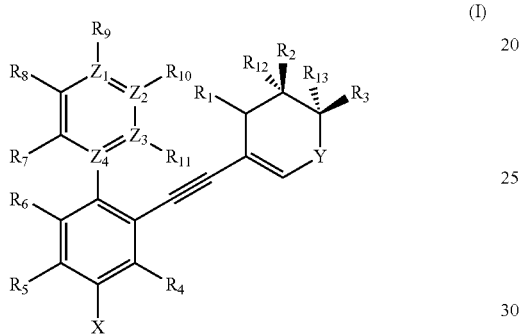

(I)

in which:
X is selected from a group consisting of biguanidine, biguanidinium ion, biguanidinium dication, guanidine, guanidnium, amine, ammonium ion, aminoalkyl, alkylammonium ion, amide, urea, amino, and hydroxyl;
Y is selected from a group consisting of methylene, methine, oxygen and amine;
$Z_1$-$Z_4$ at each occurrence are independently selected from a group consisting of nitrogen and carbon atoms;
$R_1$ is selected from a group consisting of hydrogen, methyl, amino and hydroxy;
$R_2$ and $R_3$ are independently selected from a group consisting of carboxylic acid, carboxylate ion, sulfonic acid, sulfonate ion, amide and sulfonamide;
$R_4$, $R_5$, $R_6$, and $R_7$ at each occurrence are independently selected from the group consisting of hydrogen, halogen, amino, $C_{1-12}$ alkylamino, $C_{1-12}$ alkylammonium salts, alkoxy, hydroxyl, $C_{6-24}$ aryl, $C_{3-12}$ cycloalkyl, $C_{1-12}$ alkyl, cyano and $C_{3-18}$ heteroaryl; the alkyl, aryl, heteroaryl, amino, and alkylamino groups with respect to $R_4$, $R_5$, $R_6$, and $R_7$ may be unsubstituted; the alkylamino and alkylammonium salts with respect to $R_4$, $R_5$, $R_6$, and $R_7$ may be primary, secondary, or tertiary;
$R_9$-$R_{11}$ is selected from the group consisting of buta-1,3-diyne-1-sulfonamide, penia-2,4-diynamide, hydrogen, halogen, amino, $C_{1-12}$ alkylamino, $C_{1-12}$ alkylammonium salts, alkoxy, hydroxyl, $C_{6-24}$ aryl, $C_{3-12}$ cycloalkyl, $C_{1-12}$ alkyl, cyano and $C_{3-18}$ heteroaryl; the alkyl, aryl, heteroaryl, amino, and alkylamino groups with respect to $R_8$ may be unsubstituted; the alkylamino and alkylammonium salts with respect to $R_8$ may be primary, secondary, or tertiary;
$R_9$-$R_{11}$ at each occurrence are independently selected from a group consisting of is selected from the group consisting of hydrogen, halogen, amino, $C_{1-12}$ alkylamino, $C_{1-12}$ alkylammonium salts, alkoxy, hydroxyl, $C_{6-24}$ aryl, $C_{3-12}$ cycloalkyl, $C_{1-12}$ alkyl, cyano, $C_{3-18}$ heteroaryl, and hydroxyalkyl; the alkyl, aryl, heteroaryl, amino, and alkylamino groups may be unsubstituted; the alkylamino and alkylammonium salts with respect to $R_9$-$R_{11}$ may be primary, secondary, or tertiary; and
$R_{12}$ and $R_{13}$ are independently selected from a group consisting of hydrogen, methyl, hydroxy, amino, aminoalkyl and hydroxyalkyl.

2. A compound of formula (II):

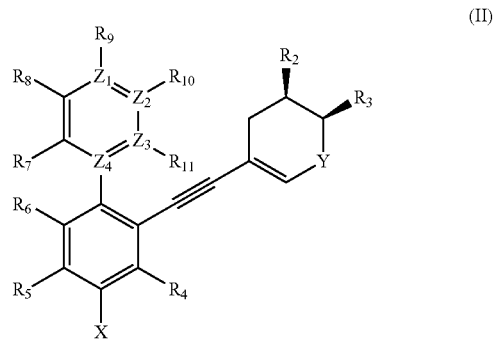

(II)

in which: X is selected from a group consisting of biguanidine, biguanidinium ion, biguanidinium dication, guanidine, guanidnium, amine, ammonium ion, aminoalkyl, alkylammonium ion, amide, urea, amino, and hydroxyl;
Y is selected from a group consisting of methylene, methine, oxygen and amine;
$Z_1$-$Z_4$ at each occurrence are independently selected from a group consisting of nitrogen and carbon atoms;
$R_2$ and $R_3$ are independently selected from a group consisting of carboxylic acid, carboxylate ion, sulfonic acid, sulfonate ion, amide and sulfonamide;
$R_4$, $R_5$, $R_6$, and $R_7$ at each occurrence are independently selected from the group consisting of hydrogen, halogen, amino, $C_{1-12}$ alkylamino, $C_{1-12}$ alkylammonium salts, alkoxy, hydroxyl, $C_{6-24}$ aryl, $C_{3-12}$ cycloalkyl, $C_{1-12}$ alkyl, cyano and $C_{3-18}$ heteroaryl; the alkyl, aryl, heteroaryl, amino, and alkylamino groups with respect to $R_4$, $R_5$, $R_6$, and $R_7$ may be unsubstituted; the alkylamino and alkylammonium salts with respect to $R_4$, $R_5$, $R_6$, and $R_7$ may be primary, secondary, or tertiary;
$R_8$ is selected from the group consisting of buta-1,3-diyne-1-sulfonamide, penta-2,4-diynamide, hydrogen, halogen, amino, $C_{1-12}$ alkylamino, $C_{1-12}$ alkylammonium salts, alkoxy, hydroxyl, $C_{6-24}$ aryl, $C_{3-12}$ cycloalkyl, $C_{1-12}$ alkyl, cyano and $C_{3-18}$ heteroaryl; the alkyl, aryl, heteroaryl, amino, and alkylamino groups with respect to $R_8$ may be unsubstituted; the alkylamino and alkylammonium salts with respect to $R_8$ may be primary, secondary, or tertiary; and
$R_9$-$R_{11}$ at each occurrence are independently selected from a group consisting of is selected from the group consisting of hydrogen, halogen, amino, $C_{1-12}$ alkylamino, $C_{1-12}$ alkylammonium salts, alkoxy, hydroxyl, $C_{6-24}$ aryl, $C_{3-12}$ cycloalkyl, $C_{1-12}$ alkyl, cyano, $C_{3-18}$ heteroaryl, and hydroxyalkyl; the alkyl, aryl, heteroaryl, amino, and alkylamino groups may be unsubstituted; the alkylamino and alkylammonium salts with respect to $R_9$-$R_{11}$ may be primary, secondary, or tertiary.

3. A compound of formula (III):

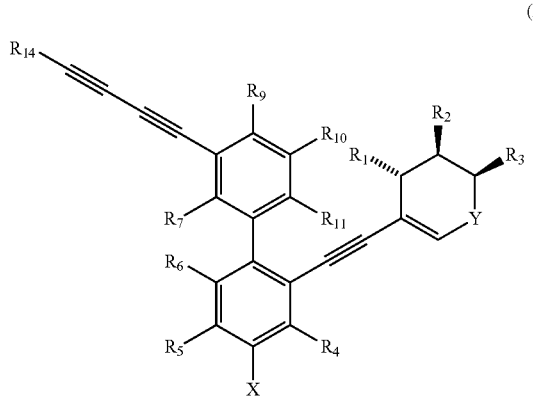

(III)

in which: X is selected from a group consisting of biguanidine, biguanidinium ion, biguanidinium dication, guanidine, guanidnium, amine, ammonium ion, aminoalkyl, alkylammonium ion, amide, urea, amino, and hydroxyl;

Y is selected from a group consisting of methylene, methine, oxygen and amine;

$Z_1$-$Z_4$ at each occurrence are independently selected from a group consisting of nitrogen and carbon atoms;

$R_2$ and $R_3$ are independently selected from a group consisting of carboxylic acid, carboxylate ion, sulfonic acid, sulfonate ion, amide and sulfonamide;

$R_4$, $R_5$, $R_6$, and $R_7$ at each occurrence are independently selected from the group consisting of hydrogen, halogen, amino, $C_{1-12}$ alkylamino, $C_{1-12}$ alkylammonium salts, alkoxy, hydroxyl, $C_{6-24}$ aryl, $C_{3-12}$ cycloalkyl, $C_{1-12}$ alkyl, cyano and $C_{3-18}$ heteroaryl; the alkyl, aryl, heteroaryl, amino, and alkylamino groups with respect to $R_4$, $R_5$, $R_6$, and $R_7$ may be unsubstituted; the alkylamino and alkylammonium salts with respect to $R_4$, $R_5$, $R_6$, and $R_7$ may be primary, secondary, or tertiary;

$R_9$-$R_{11}$ at each occurrence are independently selected from a group consisting of is selected from the group consisting of hydrogen, halogen, amino, $C_{1-12}$ alkylamino, $C_{1-22}$ alkylammonium salts, alkoxy, hydroxyl, $C_{6-24}$ aryl, $C_{3-12}$ cycloalkyl, $C_{1-12}$ alkyl, cyano, $C_{3-18}$ heteroaryl, and hydroxyalkyl; the alkyl, aryl, heteroaryl, amino, and alkylamino groups may be unsubstituted; the alkylamino and alkylammonium salts with respect to $R_9$-$R_{11}$ may be primary, secondary, or tertiary; and $R_{14}$ is selected from group consisting of amide and sulfonamide.

* * * * *